United States Patent
Hamad-Schifferli et al.

(10) Patent No.: US 8,445,228 B2
(45) Date of Patent: May 21, 2013

(54) ENHANCEMENT OF IN VITRO TRANSLATION BY NANOPARTICLE CONJUGATES

(75) Inventors: Kimberly S. Hamad-Schifferli, Somerville, MA (US); Sunho Park, Silver Spring, MD (US)

(73) Assignee: Massachusetts Institute of Technology, Cambridge, MA (US)

( * ) Notice: Subject to any disclaimer, the term of this patent is extended or adjusted under 35 U.S.C. 154(b) by 443 days.

(21) Appl. No.: 12/637,743

(22) Filed: Dec. 14, 2009

(65) Prior Publication Data

US 2011/0117597 A1    May 19, 2011

Related U.S. Application Data

(60) Provisional application No. 61/261,733, filed on Nov. 16, 2009.

(51) Int. Cl.
*C12P 21/06* (2006.01)
*C07H 21/02* (2006.01)
*C07H 21/04* (2006.01)

(52) U.S. Cl.
USPC .......................................... 435/69.1; 536/23.1

(58) Field of Classification Search ........................ None
See application file for complete search history.

(56) References Cited

U.S. PATENT DOCUMENTS

| | | | |
|---|---|---|---|
| 5,492,817 A | 2/1996 | Thompson et al. |
| 5,527,675 A | 6/1996 | Coull et al. |
| 5,539,082 A | 7/1996 | Nielsen et al. |
| 5,623,049 A | 4/1997 | Lobberding et al. |
| 5,714,331 A | 2/1998 | Buchardt et al. |
| 5,736,336 A | 4/1998 | Buchardt et al. |
| 5,773,571 A | 6/1998 | Nielsen et al. |
| 5,786,461 A | 7/1998 | Buchardt et al. |
| 6,168,931 B1 | 1/2001 | Swartz et al. |
| 6,417,340 B1 | 7/2002 | Mirkin et al. |
| 6,437,050 B1 | 8/2002 | Krom et al. |
| 6,495,324 B1 | 12/2002 | Mirkin et al. |
| 6,506,564 B1 | 1/2003 | Mirkin et al. |
| 6,582,921 B2 | 6/2003 | Mirkin et al. |
| 6,610,491 B2 | 8/2003 | Mirkin et al. |
| 6,645,721 B2 | 11/2003 | Mirkin et al. |
| 6,673,548 B2 | 1/2004 | Mirkin et al. |
| 6,677,122 B2 | 1/2004 | Mirkin et al. |
| 6,682,895 B2 | 1/2004 | Mirkin et al. |
| 6,709,825 B2 | 3/2004 | Mirkin et al. |
| 6,720,147 B2 | 4/2004 | Mirkin et al. |
| 6,720,411 B2 | 4/2004 | Mirkin et al. |
| 6,730,269 B2 | 5/2004 | Mirkin et al. |
| 6,740,491 B2 | 5/2004 | Mirkin et al. |
| 6,750,016 B2 | 6/2004 | Mirkin et al. |
| 6,759,199 B2 | 7/2004 | Mirkin et al. |
| 6,767,702 B2 | 7/2004 | Mirkin et al. |
| 6,773,884 B2 | 8/2004 | Mirkin et al. |
| 6,777,186 B2 | 8/2004 | Mirkin et al. |
| 6,828,432 B2 | 12/2004 | Mirkin et al. |
| 6,872,450 B2 | 3/2005 | Liu et al. |
| 6,902,895 B2 | 6/2005 | Mirkin et al. |
| 6,903,207 B2 | 6/2005 | Mirkin et al. |
| 2003/0143604 A1* | 7/2003 | Storhoff et al. ................... 435/6 |
| 2003/0147966 A1 | 8/2003 | Franzen et al. |
| 2003/0166054 A1 | 9/2003 | Lee et al. |
| 2006/0211083 A1 | 9/2006 | Katzen et al. |
| 2009/0209629 A1 | 8/2009 | Mirkin et al. |

OTHER PUBLICATIONS

Zanchet et al., Electrophoretic and Structural Studies of DNA-Directed Au Nanoparticle Groupings, Journal of Physical Chemistry B 106:11758-11763 (2002).
Ahmadi, T. S. et al., Shape-Controlled Synthesis of Colloidal Platinum Nanoparticles, Science, 272:1924-1926 (1996).
Demers et al., A Fluorescence-Based Method for Determining the Surface Coverage and Hybridization Efficiency of Thiol-Capped Oligonucleotides Bound to Gold Thin Films and Nanoparticles, Analytical Chemistry, 72:5535-5541 (2000).
Fraser, C. S. et al., Structural and Mechanistic Insights into Hepatitis C Viral Translation Initiation. Nature Reviews Microbiology 5:29-38 (2007).
Green et al., Simple conjugated polymer nanoparticles as biological labels, Proc. R. Soc. A, 465:2751-2759 (2009).
Park, et al., Changes in oligonucleotide conformation on nanoparticle surfaces by modification with mercaptohexanol, Nano Letters 4:1925-1929 (2004).
Shtykova, et al., Structure and Properties of Iron Oxide Nanoparticles Encapsulated by Phospholipids with Poly(ethylene glycol) Tails J. Phys. Chem., 111:18078-18086 (2007).
Srinivasan, et al., Synthesis of Fluorescent DNA-Modified Polymer Nanoparticles for Use in a Highly Sensitive DNA Detection Assay, Nanoscape 6(1), Summer 2009, on the World Wide Web at nanoscape(.)northwestern(.)edu.
Zanchet et al., Electrophoretic isolation of discrete Au nanocrystal/DNA conjugates, Nano Letters 1:32-35 (2001).

* cited by examiner

*Primary Examiner* — Nancy T Vogel
(74) *Attorney, Agent, or Firm* — McCarter & English, LLP

(57) ABSTRACT

Provided herein are kits and methods suitable for enhancing in vitro translation of a nuclei acid sequence of interest.

19 Claims, 20 Drawing Sheets

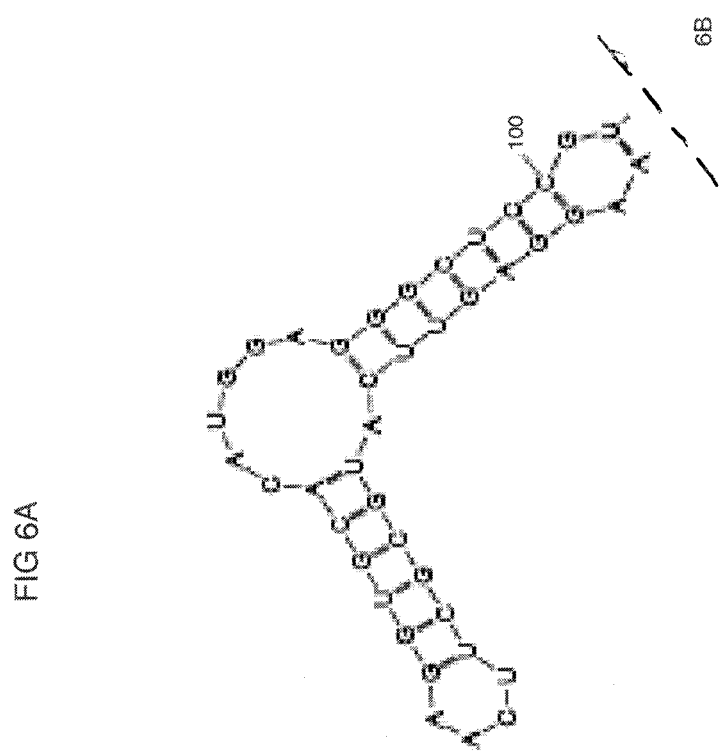

FIG. 11
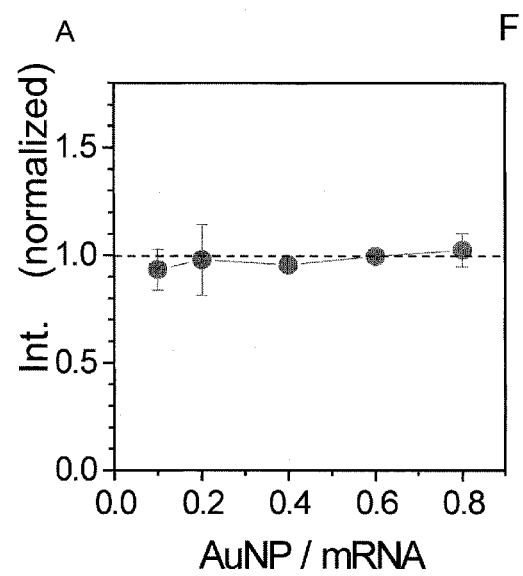
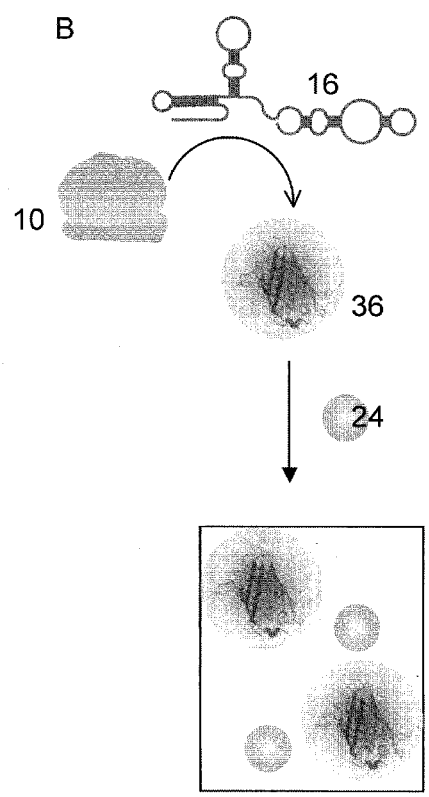

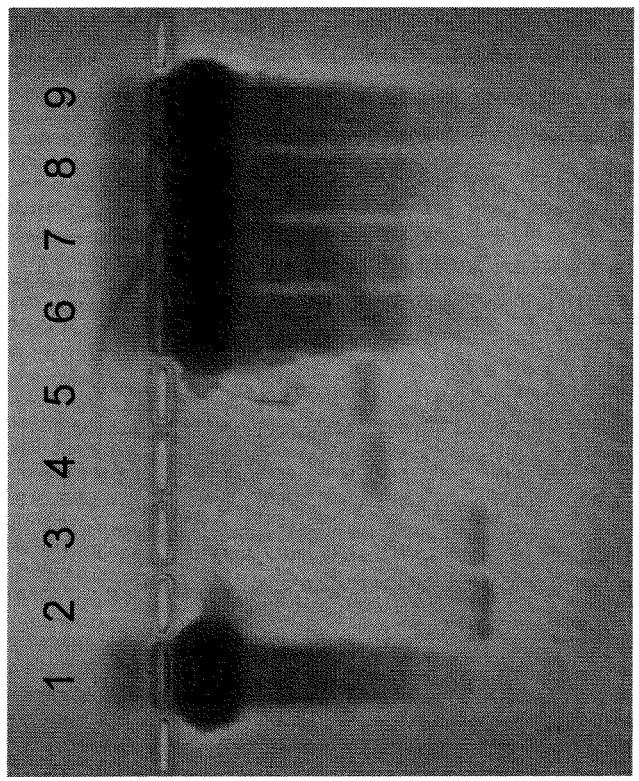
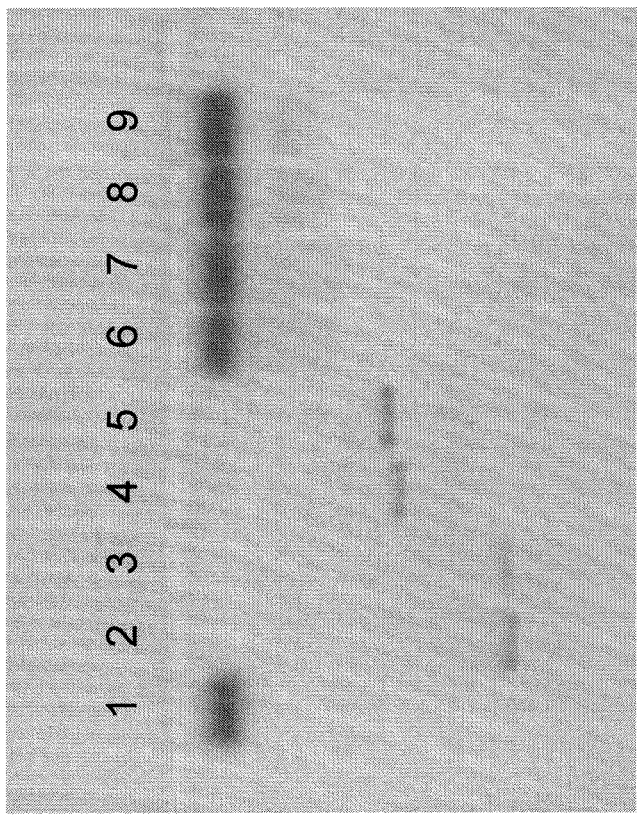
FIG. 12

FIG. 16
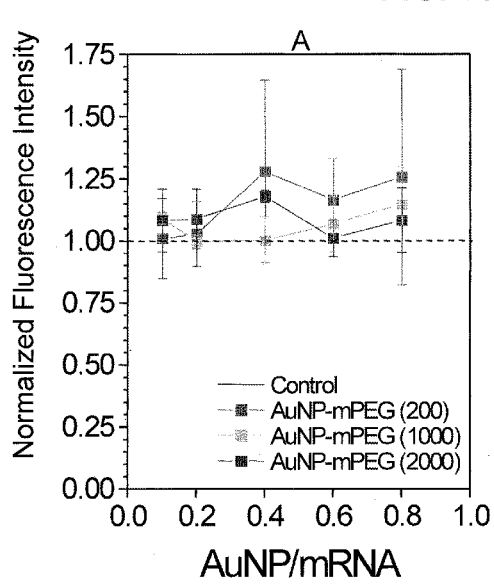 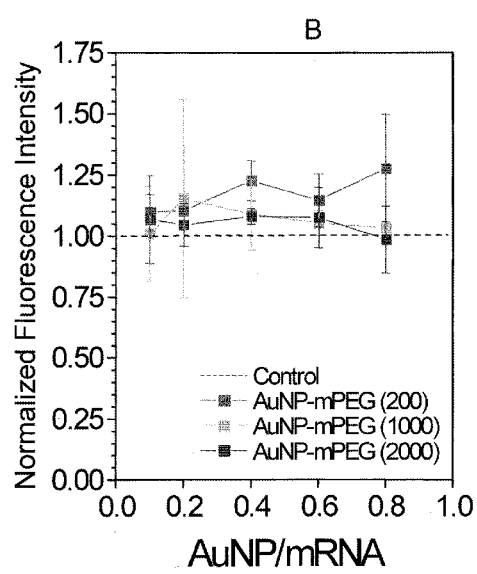

ENHANCEMENT OF IN VITRO TRANSLATION BY NANOPARTICLE CONJUGATES

RELATED APPLICATIONS

This application claims the benefit of priority to U.S. application 61/261,733, filed Nov. 16, 2009, the teachings of which are incorporated herein in their entirety.

GOVERNMENT FUNDING

This invention was made with government support under grant number R21 EB008156 awarded by the National Institutes of Health. The government has certain rights in this invention.

BACKGROUND OF THE TECHNOLOGY

In vitro translation is an important tool for research in molecular biology, diagnostic assays, and biological discovery. Commercially available cell free lysate kits work by supplying a cell free lysate that contains most if not all of the cellular components necessary to translate mRNA to which the user adds DNA or mRNA encoding a protein of interest. These in vitro translation kits have enabled biological discovery for important ramifications in health care, drug design, and biological sensing. Under conditions suitable for translation to occur, the protein of interest is synthesized using translation machinery provided by the lysate. However, one serious limitation of currently available methods of in vitro translation is the amount of protein that is produced. Many kits and/or methods suffer from low and unreliable protein production. Because mRNA can be easily degraded by numerous mechanisms, mRNA lifetime is viewed as one limiting factor of current in vitro translation methods. Current strategies for improving protein production typically focus on increasing mRNA stability and resistance to degradation. However, translation is a complex process, involving not only mRNA but also multiple translation factors, all of which must be coordinated. In particular, initiation, a complex first step of translation, requires numerous initiation factors to be brought in close proximity of the mRNA, the ribosome, and one another. As a result the process in vitro is very inefficient and produces little protein.

As shown in FIG. 2, the biological process of translation, that is, synthesis of a specific protein encoded in a particular mRNA is a complicated process involving hundreds of different components.[5] The different components interact with each other and the mRNA in a coordinated fashion to synthesize the protein encoded by the mRNA.

Translation can be conducted in the absence of cells (in vitro) and is a central biological tool that is used in many areas of bioengineering and biological research. In vitro translation is used to produce specific proteins of interest from nucleic acid sequences encoding them, in the engineering of proteins for pharmaceutical, diagnostic, and research tool use, as well as in the search and discovery of proteins. To reproduce this complicated biological process in the laboratory setting, the many biological components shown in FIG. 2 must be provided to the reaction. Such translation components are provided in the form of kits. However, even with the use of kits, in vitro translation is highly inefficient and typically produces very small quantities of protein product.

SUMMARY

Provided herein are kits and methods suitable for enhancing in vitro translation of a nuclei acid sequence of interest.

In some embodiments, kits provided herein comprise nanoparticles and one or more reagents for conducting in vitro translation of a nucleic acid sequence. In some embodiments, one or more compounds coat or are conjugated to the nanoparticles. In some embodiments, the nanoparticles and one or more compounds are provided separately and instructions for coating the nanoparticles with the one or more compounds or conjugating the one or more compounds to the nanoparticles are provided. In some embodiments, the presence of the one or more compounds conjugated to nanoparticles enhances the in vitro translation of the nucleic acid sequence compared to in vitro translation in the absence of conjugated nanoparticles.

In some embodiments, kits provided herein comprise nanoparticles, directions for conjugating one or more compounds to the nanoparticles, and one or more reagents for conducting in vitro translation.

In some embodiments, the compound is a nucleobase. In some embodiments, the compound is polyethylene glycol.

Methods for in vitro translation of a nuclei acid sequence are provided herein. In some embodiments, the method comprises contacting nanoparticles with a nucleic acid sequence of interest to be translated and with a reagent for conducting in vitro translation. In some embodiments, the nanoparticles are coated with or conjugated to a compound as described, herein. In some embodiments, the method includes the step of coating or conjugating the nanoparticles with the compound.

The various embodiments described herein can be complimentary and can be combined or used together in a manner understood by the skilled person in view of the teachings contained herein.

BRIEF DESCRIPTION OF FIGURES

FIG. 11 is a graph (A) and schematic diagram (B) of a control in vitro translation reaction where free NP have been added to the reaction product.

FIG. 12 shows a picture of an agarose gel before (left) and after stained with coomassie blue (right).

FIG. 16 shows a schematic diagram of an NP-conjugate wherein the conjugated compound is mPEG and the results of in vitro translation carried out in the presence of NP-mPEG prepared by reacting NP with free mPEG at NP to mPEG ratios of 1:200, 1000 or 2000, respectively (dark grey, light gray, and black squares, respectively) at the indicated NP-conjugate:mRNA ratios using GFP encoding mRNA (right graph) and mCherry encoding mRNA (left graph).

DETAILED DESCRIPTION OF THE TECHNOLOGY

Figure 1:
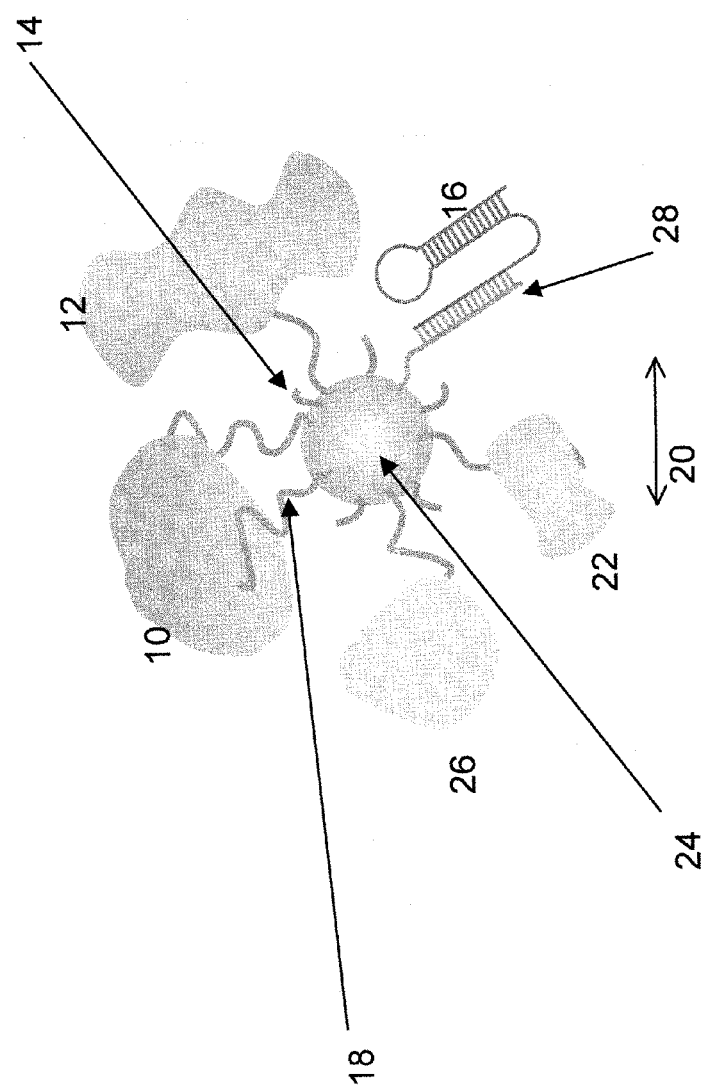
FIG. 1 is a schematic diagram showing NP conjugates, such as NP-DNA conjugates, added to in vitro translation mixes and binding to mRNA and recruiting translation machinery.
Figure 2:
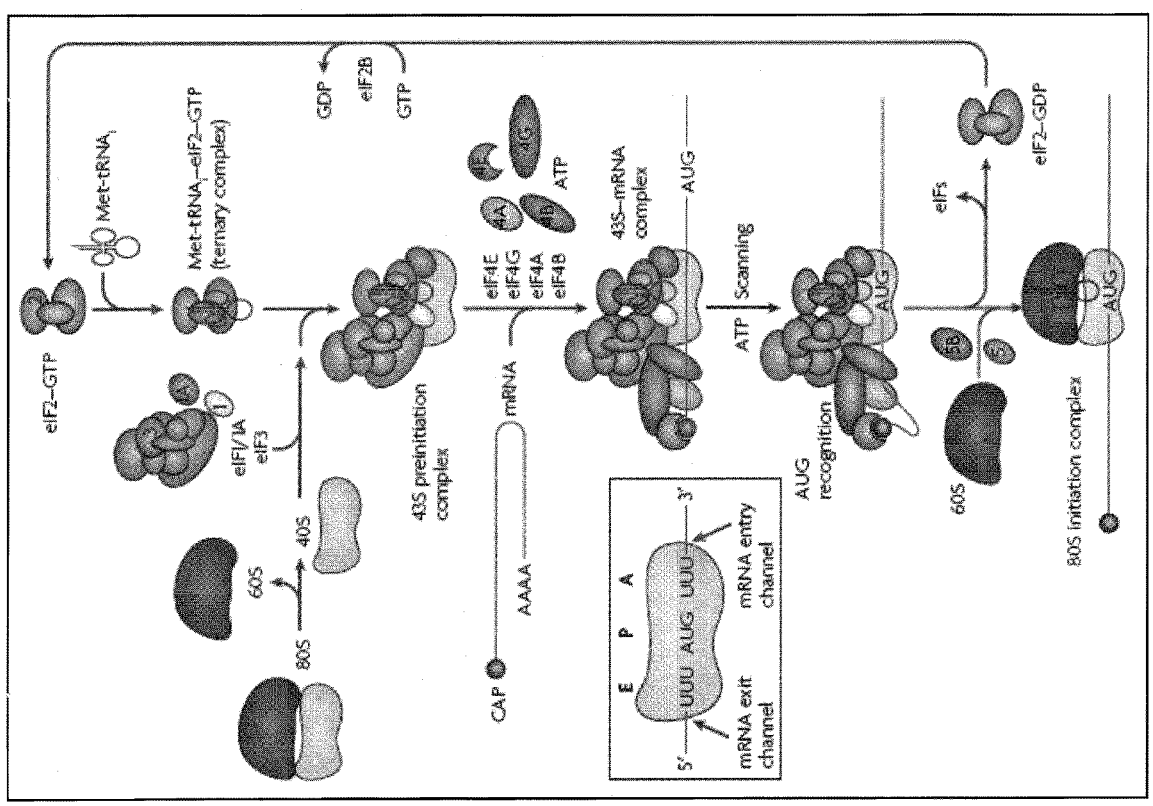
FIG. 2 is a schematic diagram showing the cellular process and machinery for translation.
Figure 3:
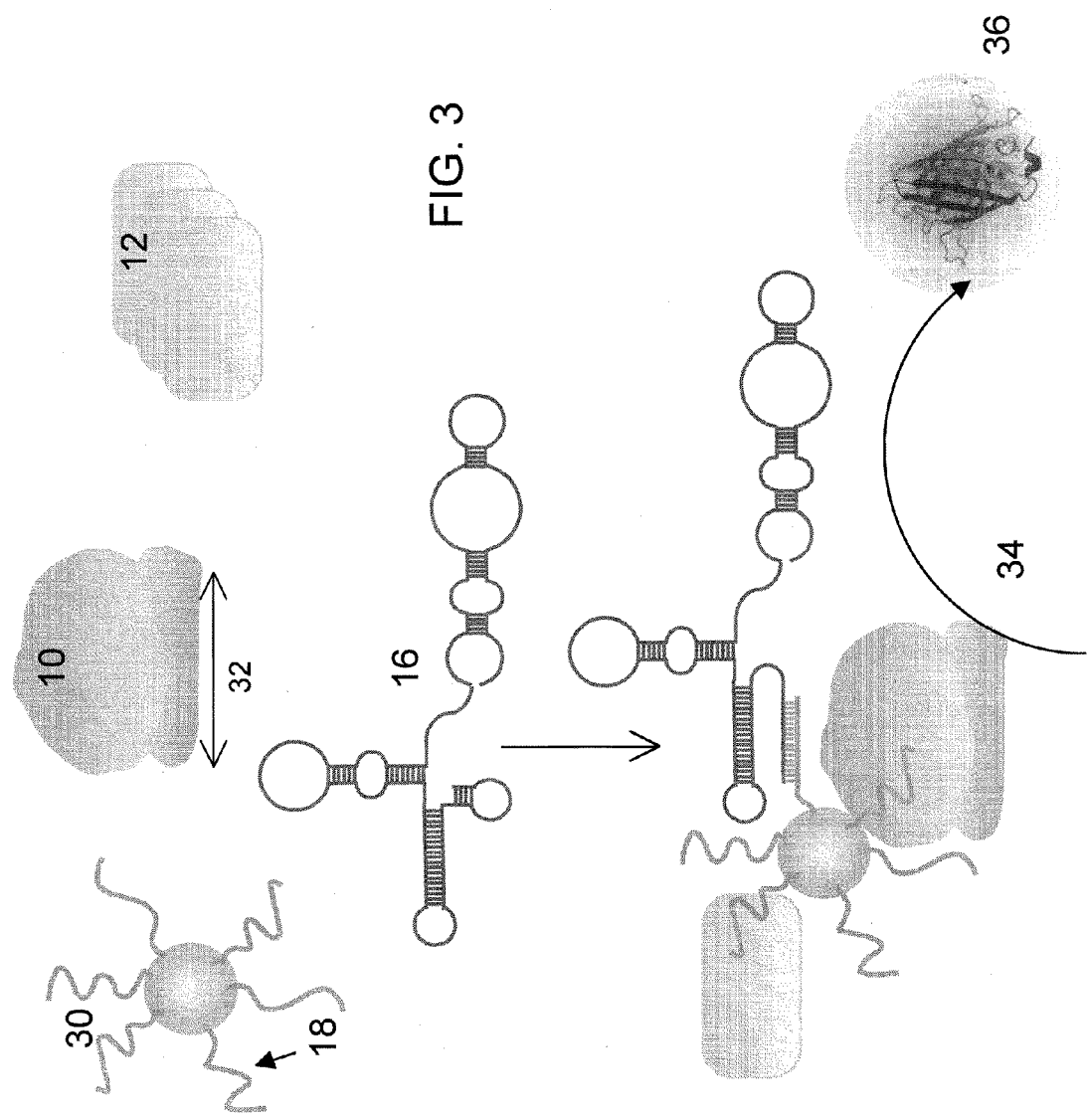
FIG. 3 is a schematic diagram showing a simplified view of the process of translation.

As demonstrated herein, nanoparticle conjugates can be used to enhance the process of in vitro translation of nucleic acid sequences such as mRNA. As shown in FIG. 3, the process of translation involves an mRNA 16 that encodes a protein of interest, the ribosome 10, various translation factors (eIFs) 12 and tRNAs, which are not shown. The eIFs ribosome, tRNAs, etc. interact with each other rather weakly. In addition, ability of the nanoparticles provided herein to enhance in vitro translation was unexpected. Due to their size, nanoparticles were expected to increase steric hindrance with the similarly sized ribosome and physically block the ribosome from reading the mRNA. The steric hindrance was expected to result in inhibition of the translation reaction by physically blocking the ribosome in a way that results in less protein translation. However, conjugation of the DNA to the nanoparticle apparently changes the DNA's ability to bind to the mRNA, decreasing the binding strength. It was unexpectedly found that the nanoparticle does not act as a steric barrier. Furthermore, the nanoparticles provided herein were found to interact with the reaction components (such as ribosomes, eIFs, and the like) strongly enough to co-localize the reaction components with the mRNA to enhance translation.

Without wishing to be bound by theory, it is thought that nanoparticle conjugates provided herein recruit or otherwise aggregate one or more components of a complex biological reaction such as the machinery involved in translation. The nanoparticles may be acting as a "scaffold," or a system that brings together the different components involved in a biological reaction such as in vitro translation. The nanoparticle conjugates provided herein allow, for example, the translation machinery a greater chance of initiating and/or maintaining translation of the mRNA. The recruitment is thought to be due to interactions between one or more of the reaction components and the NP-conjugate. It is thought that the nanoparticles provided herein are ideal for bringing the various in reaction components together in close spatial proximity thereby enhancing the rate of the reaction. As shown herein, many proteins of the reaction and DNA weakly bind to nanoparticles through "sticking" or "non-specific adsorption," this allows the ribosome and translation factors to come on and off the nanoparticle, thereby enhancing the overall efficiency of the reaction.

Typically when nanoparticles are used to bind to specific species such as nucleic acids and proteins, the nanoparticles are coated or conjugated with binding moieties such as aptamers/peptides/antibodies that are designed to strongly bind the target. However, in this case this would not be feasible for enhancement of in vitro translation, as strong binding between the nanoparticle and the reaction components would not allow the components to come on and off the particle, which is essential for the reaction to proceed. Therefore, the ability of the nanoparticles to bind non-covalently and/or weakly to multiple proteins and nucleic acids of the reaction allows their use as a nanoscale "platform" for a reaction.

In some embodiments, the stronger interactions are due in part to the interaction between the component conjugated to the nanoparticle and the mRNA. For example, where the conjugated component is a nucleobase sequence such as DNA, the nucleobase sequence can be designed to have a sequence that is complementary to at least a portion of the user defined or user specified mRNA sequence. In addition, a conjugated component that confers an overall positive charge on the nanoparticle conjugate can allow stronger interaction between the NP-conjugate and the negatively charged mRNA.

Kits and reagents are provided herein that can be used in in vitro translation reactions to enhance the translation of a user specified mRNA. In some embodiments, the kits comprise nanoparticles (NPs) and one or more reagents for conducting in vitro translation of a nucleic acid sequence. In some embodiments, one or more compounds coat or are conjugated to the NPs. In some embodiments, the NPs and one or more compounds are provided separately and instructions for coating the NPs with the one or more compounds or conjugating the one or more compounds to the NPs are provided. In some embodiments, the presence of the one or more compounds conjugated to NPs enhances the in vitro translation of the nucleic acid sequence compared to in vitro translation in the absence of conjugated NPs. The NPs or conjugated NPs of the kits provided herein can be supplied in a single tube to be dispensed by the user. The NPs or conjugated NPs of the kits provided herein can be supplied in a manner that is suitable for high throughput use, for example the NPs or conjugated NPs can be supplied as ready-to-use portions in a multi-well plate.

In some embodiments, kits provided herein comprise NPs, directions for conjugating one or more compounds to the NPs, and one or more reagents for conducting in vitro translation.

In some embodiments, the compound provided in the kit is a nucleobase sequence. In some embodiments, the compound provided in the kit is polyethylene glycol.

Methods for in vitro translation of a nuclei acid sequence are provided herein. In some embodiments, the method comprises contacting NPs with a nucleic acid sequence of interest to be translated and with a reagent for conducting in vitro translation. In some embodiments, the NPs are coated with or conjugated to a compound as described, herein. In some embodiments, the method includes the step of coating or conjugating the NPs with the compound.

Nanoparticles

NPs for use in the methods and kits provided herein can be composed of any suitable material that allows the NP to be conjugated with a compound such as a nucleobase sequence or polyethylene glycol and used in an in vitro translation reaction. Suitable materials include, for example, polymers, metals such as gold, silver, copper, or platinum; semiconductor materials such as CdSe, CdS, CdS or CdSe coated with ZnS, magnetic (e.g., ferromagnetite) colloidal materials, metal oxide materials such as ZnO, and $TiO_2$ and other metal materials such as ZnS, AgI, AgBr, $HgI_2$, PbS, PbSe, ZnTe, CdTe, $In_2$, $Se_3$, $Cd_3$, $P_2$, $Cd_{3, As2}$, InAs, and GaAs.

Methods of making metal, semiconductor and magnetic nanoparticles are well known in the art. See, e.g., Schmid, G. (ed.) Clusters and Colloids (VCH, Weinheim, 1994); Hayat, M. A. (ed.) Colloidal Gold: Principles, Methods, and Applications (Academic Press, San Diego, 1991); Massart, R., IEEE Taransactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988). Methods of making ZnS, ZnO, $TiO_2$, AgI, AgBr, $HgI_2$, PbS, PbSe, ZnTe, CdTe, $In_2$, $S_3$, $In_2$, $Se_a$, $Cd_3$, $P_2$, $Cd_3$, $As_2$, InAs, and GaAs nanoparticles are also known in the art. See, e.g., Weller, Angew. Chem. Int. Ed. Engl., 32, 41 (1993); Henglein, Top. Curr. Chem., 143, 113 (1988); Henglein, Chem. Rev., 89, 1861 (1989); Brus, Appl. Phys. A., 53, 465 (1991); Bahncmann, in Photochemical Conversion and Storage of Solar Energy (eds. Pelizetti and Schiavello 1991; Wang and Herron, J. Phys. Chem., 95, 525 (1991); Olshaysky et al., J. Am. Chem. Soc., 112, 9438 (1990); Ushida et al., J. Phys. Chem., 95, 5382 (1992).

Suitable NPs can be composed of polymers. See U.S. Pat. No. 6,437,050 to Krom, et al., Srinivasan, et al., Synthesis of Fluorescent DNA-Modified Polymer Nanoparticles for Use in a Highly Sensitive DNA Detection Assay, Nanoscape 6(1), Summer 2009, on the World Wide Web at nanoscape(.)northwestern(.)edu. Suitable nanoparticles are also commercially available from, e.g., Ted Pella, Inc., Amersham Corporation, and Nanoprobes, Inc.

NPs suitable for the methods and kits provided herein can have a size range of about 1 nm to about 500 nm (mean diameter). In some embodiments, the mean diameter is about 5 to about 100. In other embodiments, the mean diameter is about 5 to about 50 nm. In other embodiments, the mean diameter is about 5 to about 25 nm. In other embodiments, the mean diameter is about 5 to about 10 nm. The size of the NP can be chosen that enhances protein production the in vitro translation reaction using NP of differing sizes, conjugating the NPs to a given compound (as provided herein) and determining which size of conjugated NP yields the largest enhancement in protein production. The size of the NP can be changed using methods know in the art for the given NP material. For example, by varying the amount of tannic acid, the size of Au NPs can be altered. Smaller NPs are produced when more tannic acid is used.

The NPs can be used in in vitro translation reactions in solution, as part of a slurry, or in batch or column mode. Where the reaction is in solution, the NPs can be soluble. Soluble NPs typically have a diameter of 100 nm or less.

In some embodiments, the NPs are coated or linked to a ligand. Suitable ligands are those that can be used to conjugate one or more compounds to the NP. In some embodiments, the ligand is a positively charged ligand. In some embodiments, the ligand is a negatively charged ligand such as BPS (bis(p-sulfonatophenyl)phenylphosphine). Other suitable coating ligands include compounds that covalently bind to the nanoparticle via a thiol, phosphine, or carboxylate, such as alkanethiol compounds and acid-terminated alkanethiol compounds. Other suitable ligands include compounds that coat or cloak the nanoparticle, for example by intercalating into an existing layer. Such ligands include phospholipids (see, for example, Shtykova, et al J. Phys. Chem., 111:18078-18086 (2007)). Suitable coating ligands also include polymers that are polymerized onto the nanoparticle, such as diblock copolymers. See U.S. Pat. No. 6,872, 450.

Conjugated Compounds

Nucleobase Sequence

As used herein, a nucleobase sequence is any oligomer comprising two or more nucleobase containing subunits (RNA, DNA, PNA), suitable for hybridizing to a target nucleic acid sequence (DNA or RNA).

Peptide Nucleic Acid (PNA) is a non-naturally occurring polyamide (pseudopeptide) which can hybridize to nucleic acid (DNA and RNA) with sequence specificity (See U.S. Pat. Nos. 5,539,082, 5,527,675, 5,623,049, 5,714,331, 5,736,336, 5,773,571, 5,786,461 and Egholm et al., Nature 365: 566-568 (1993)). Being non-naturally occurring molecules, PNAs are not known to be substrates for the enzymes, which are known to degrade peptides or nucleic acids. Therefore, PNAs should be stable in biological samples, as well as have a long shelf life. Likewise, when complexed to a nucleic acid, PNAs shield the nucleic acid from degradation (See: PCT publication WO95/15974).

In some embodiments, the NPs are conjugated to a (e.g., one or more) nucleobase strand(s). In some embodiments, the nucleobase strands conjugated to the NP have identical sequences. In some embodiments the nucleobase strands conjugated to the NP have different sequences. Nucleobase sequences suitable for use in the methods and kits provided herein are capable of binding to or interacting with one or more target sequences selected by the user. In some embodiments, the target sequence is at least a portion of the mRNA to be used as the template in the in vitro translation reaction. In some embodiments, the nucleobase conjugated to the NP surface has a sequence that is complementary to at least some section of the mRNA of interest. Nucleobase sequences suitable for use in the methods and kits provided herein have a length that is sufficient to allow hybridization between the nucleobase sequence and a complementary sequence within the target mRNA such that transcription of the target mRNA is enhanced in the presence of the NP-nucleobase sequence conjugate. In some embodiments, suitable nucleobase sequences have a length of about 3 to about 500 bases. In some embodiments, suitable nucleobase sequences have a length of about 5 to about 100 bases. In some embodiments, suitable nucleobase sequences have a length of about 10 to about 50 bases. The some embodiments, suitable nucleobase sequences have a length of about 15 to about 30 nucleobases. In some embodiments, suitable nucleobase sequences have a length of about 25 nucleobases. In some embodiments, suitable nucleobase sequences have a sequence of about 10 nucleobases. In some embodiments, transcription of the target mRNA is enhanced in the presence of the NP-conjugates provided herein even where other, non-target mRNA molecules are present in the reaction mixture.

The nucleobase sequence can be designed to hybridize to a coding region of the template nucleic acid sequence. In other embodiments, the nucleobase sequence can be designed to hybridize to a non-coding region of the mRNA. For example, the nucleobase sequence can be designed to hybridize to the sequences in the 5' or 3' UTR of the mRNA. In other embodiments, the nucleobase sequence can be designed to hybridize to an area of the mRNA that is common to mRNAs. For example, many mRNA sequences have a Kozak sequence; the nucleobase sequence can be designed to hybridize to the Kozak sequence. A nucleobase sequence that is capable of hybridizing to a common sequence among mRNAs can be used to enhance expression of any protein or more than one protein as long as the mRNA(s) has/have a site where the nucleobase sequence can hybridize. In this manner, the methods and kits provided herein can be provided with a generalized nucleobase sequence that is capable of enhancing translation of many different user defined mRNAs, without regard to the coding sequence of the mRNA of interest.

Figure 6B:
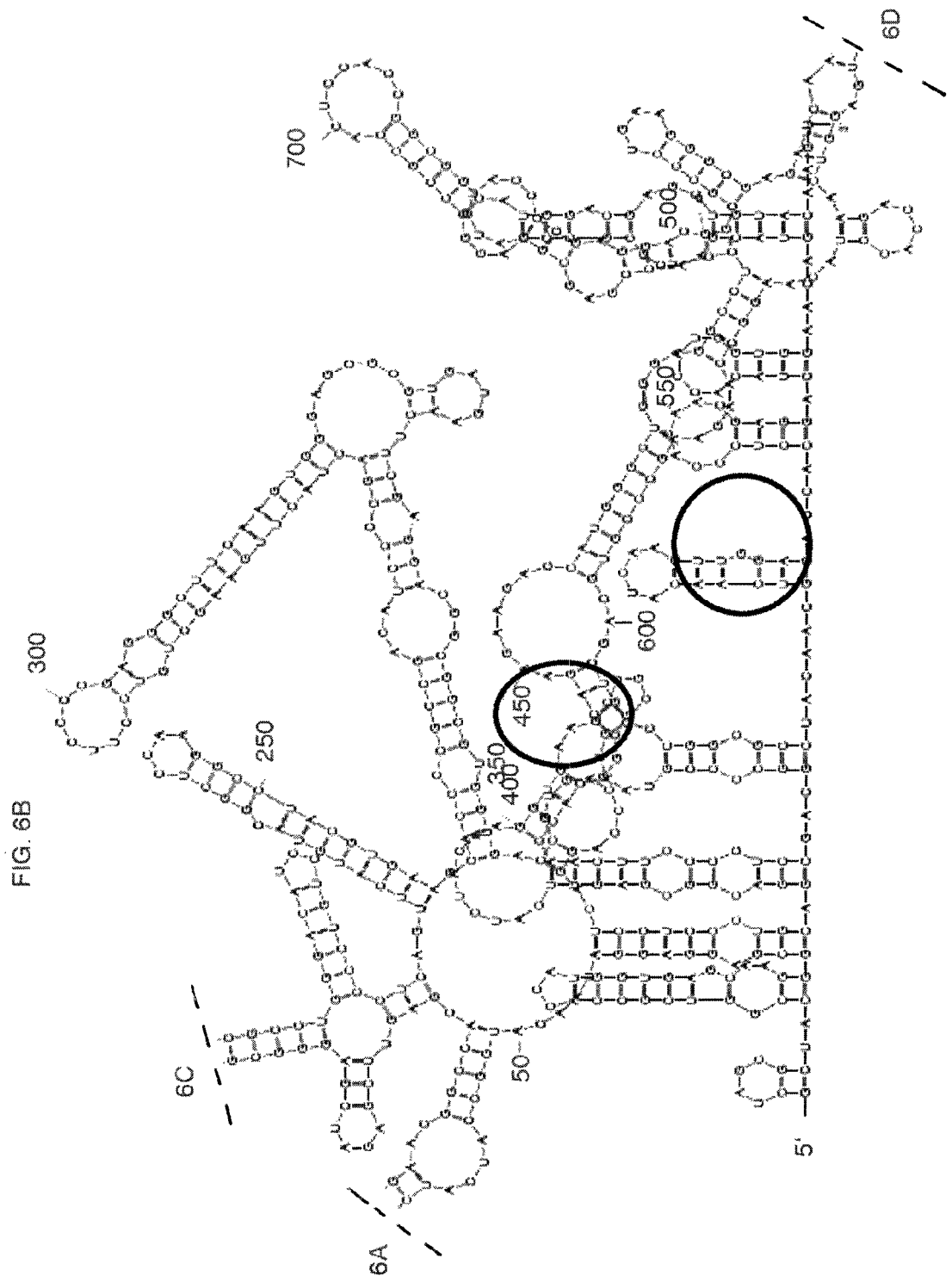
FIGS. 6A-E: show diagrams (6A-6D) of the mRNA encoding mCherry (SEQ ID NO: 4) and an example of sequences (SEQ ID NO: 5 and SEQ ID NO: 6) that would allow weak binding to a homologous DNA sequence (SEQ ID NO: 1 and SEQ ID NO: 2) (6E).
Figure 6C:
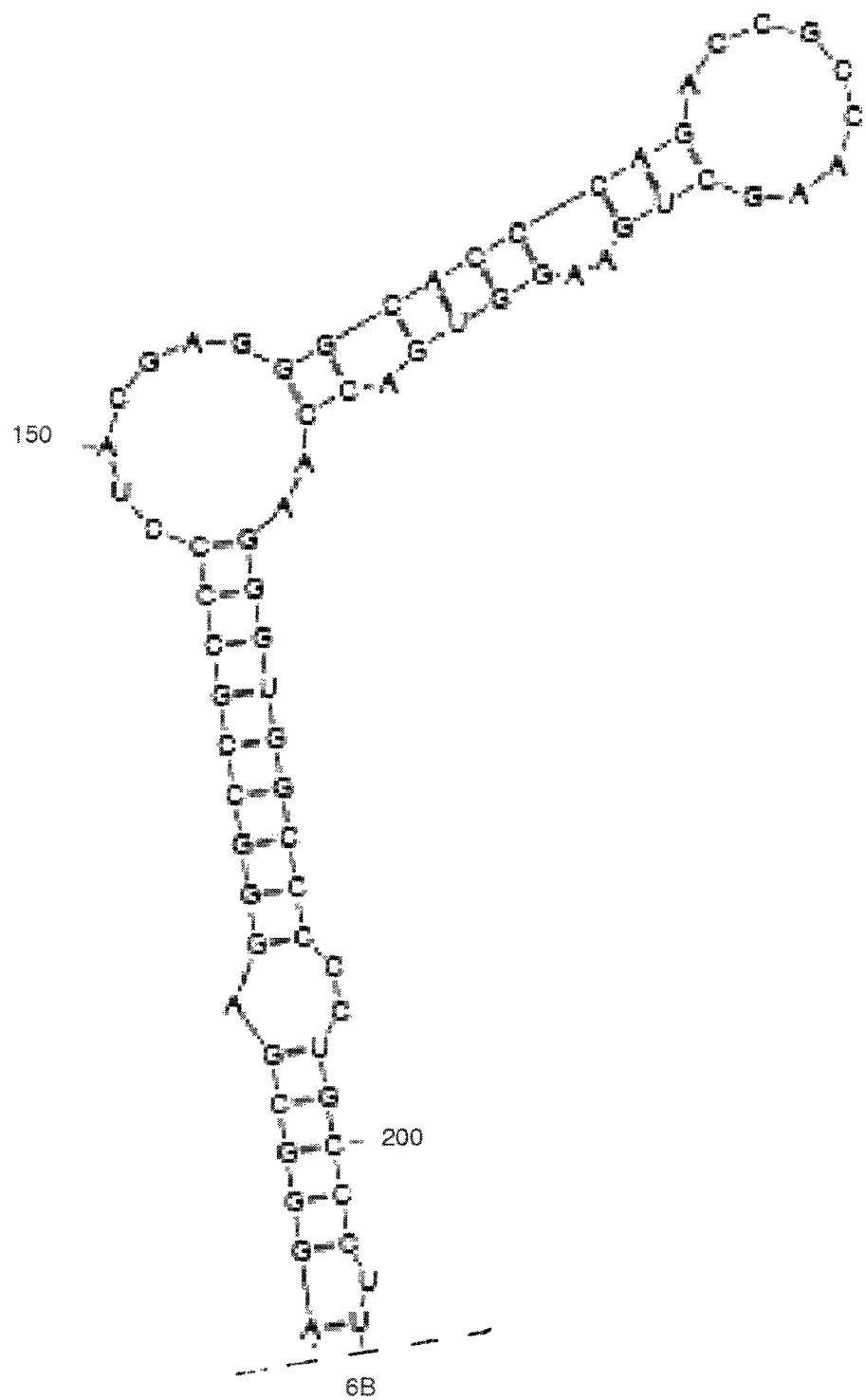
Figure 6D:
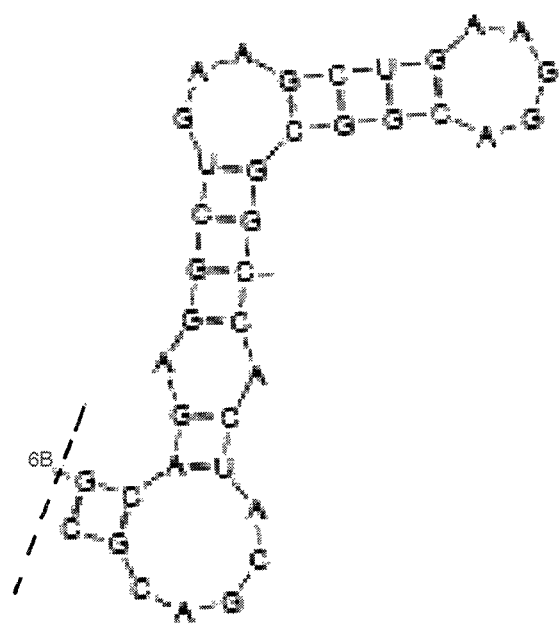
Figure 6:
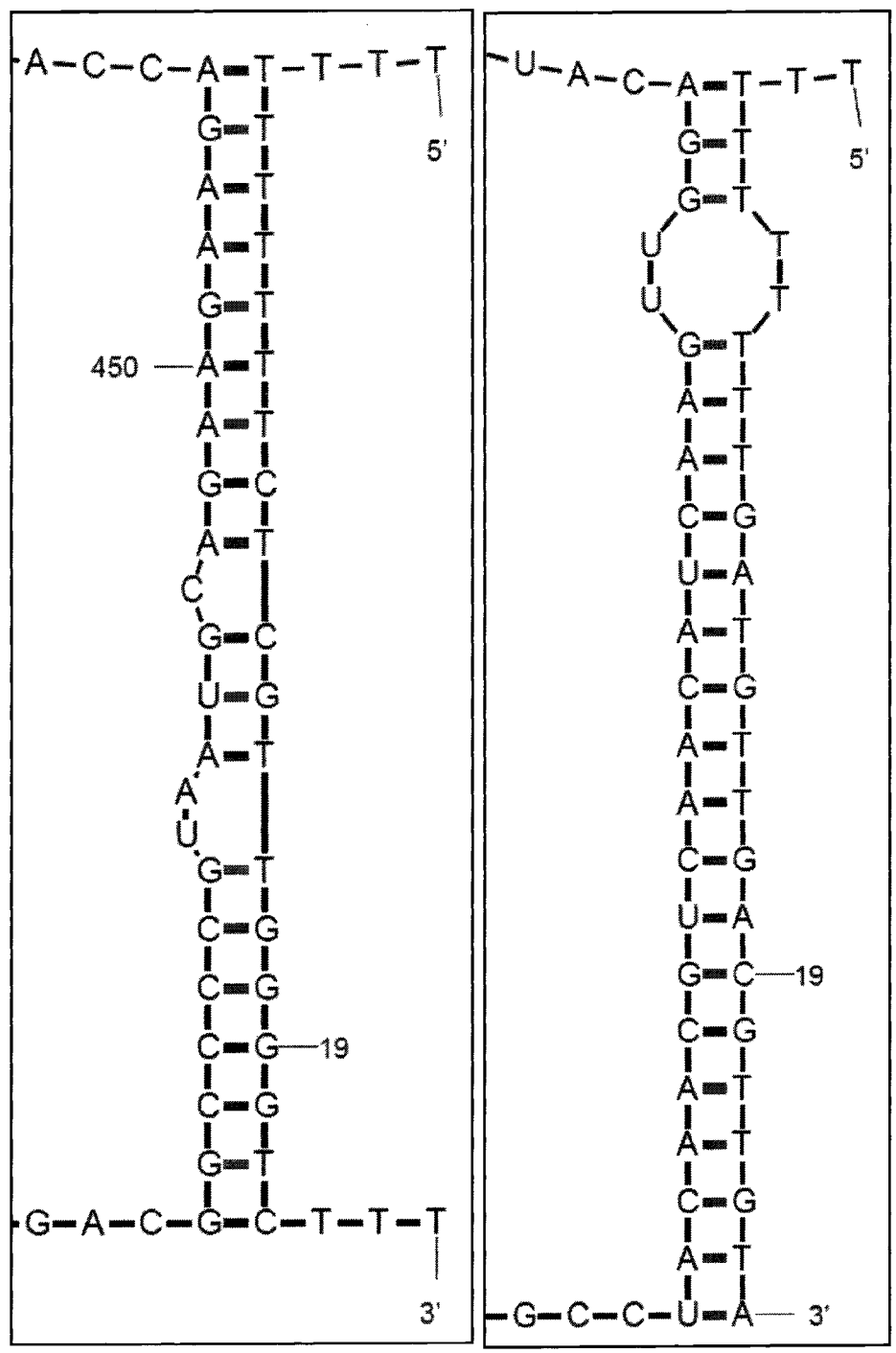

The nucleobase sequence can be designed to have a stronger or weaker binding affinity to the target nucleic acid using techniques known in the art. While nucleobase sequences having stronger binding affinity show a greater level of enhancement of in vitro translation, nucleobase sequences having a lower binding affinity also show enhancement of in vitro translation (FIG. 6).

In some embodiments, the nucleobase sequence comprises DNA or RNA. Methods of producing DNA and/or RNA molecules having a user specified sequence (such as a sequence that is complementary to at least a portion of the mRNA selected by the user) are well known in the art and include PCR, chemical synthesis, and recombinant molecular biology. In addition, RNA molecules can be produced in vitro by reverse transcription of a DNA template.

In some embodiments, the nucleobase sequence comprises PNA. Methods for the chemical assembly of PNAs are well known (See: U.S. Pat. No. 5,539,082, 5,527,675, 5,623,049, 5,714,331, 5,736,336, 5,773,571 or 5,786,571).

In some embodiments, nucleobase sequences are conjugated to the NPs. As described herein, in some embodiments, the nucleobase sequence can be chemically modified on its 3' or 5' terminus to include a reactive group that can be use to generate a covalent linkage with a ligand present on the NP. The ligand comprises a counterpart reactive group such that when the nucleobase sequence and the NP are incubated together under reactive conditions, a covalent linkage is formed between the nucleobase sequence and the NP. In some embodiments, the reactive group is a sulfur containing group and the NPs have bis(p-sulfonatophenyl)phenylphosphine dihydrate ligands on their surfaces. The nucleobase and NP are incubated together under conditions suitable to allow the formation of a thiol linkage between the nucleobase sequence and the NP.

For use in the methods and kits provided herein, the nucleobase sequences can be conjugated to the NPs at a variety of ratios of nucleobase strands to NP. A suitable ratio can be determined by preparing NP-nucleobase conjugates at different ratios of nucleobase strands per NP and then determining which ratio produced NP-nucleobase conjugates showing the largest enhancement of in vitro translation using the reactions described herein. The ratio of nucleobase strands per NP can be varied by varying the ratios of nucleobase strands to NP in the conjugation reaction. In some embodiments, the NP-nucleobase conjugate has a ratio of about 5 to about 500 strands per NP. In other embodiments, the NP-nucleobase conjugate has a ratio of about 10 to about 100 strands per NP. In other embodiments, the NP-nucleobase conjugate has a ratio of about 20 to about 70 strands per NP. In other embodiments, the NP-nucleobase conjugate has a ratio of about 10, 20, 30, 40, 50, 60, or 70 strands per NP.

Other Conjugates

In some embodiments, the NP is conjugated with a compound that reduces the charge of the NP. In some embodiments, reducing the charge of the NP is accomplished by reacting or replacing the negative ligand (such as a BPS ligand) with a neutral polymer or a polymer having less charge than the ligand. In some embodiments, the NP is conjugated to a polymer. In some embodiments, the polymer is polyethylene glycol (PEG). As described herein, in some embodiments, PEG chains comprise a reactive group that can form a covalent linkage with NPs that include a ligand having a counterpart reactive group. When the PEG and the NP are incubated together under reactive conditions, a covalent linkage is formed between the PEG and the NP. In some embodiments, the reactive group is a sulfur containing group and the NPs have bis(p-sulfonatophenyl)phenylphosphine dihydrate ligands on their surfaces. The PEG and NP are incubated together under conditions suitable to allow the formation of a thiol linkage between the PEG and the NP.

For use in the methods and kits provided herein, PEG can be conjugated to the NPs at a variety of ratios of PEG strands to NP. A suitable ratio can be determined by preparing NP-PEG conjugates at different ratios of PEG strands per NP and then determining which ratio produced NP-PEG conjugates that show the largest enhancement of in vitro translation using the reactions described herein. The ratio of PEG strands per NP can be varied by varying the ratios of PEG to NP in the conjugation reaction. In some embodiments, the NP-PEG conjugate has a ratio of about 10 to about 500 strands per NP. In other embodiments, the NP-PEG conjugate has a ratio of about 50 to about 300 strand per NP. In other embodiments, the NP-PEG conjugate has a ratio of about 100, 120, 140, 160, 180, or 200 strands per NP.

Suitable PEG strands for use in the methods and kits provided herein have a molecular weight of 50 to 2000 g/mol. In some embodiments, the PEG strands have a molecular weight of 100 to 1000 g/mol. In other embodiments, the PEG strands have a molecular weight of 200 to 500 g/mol.

In Vitro Translation

In some embodiments, the methods and kits provided herein comprise one or more in vitro translation reagents. Methods of preparing in vitro translation reagents from cell lysates are well known in the art. In addition, in vitro translation reagents are commercially available, for example, Retic Lysate IVT™ Kit, Ambion; Rabbit Reticulocyte Lysate System, GE Healthcare; Canine Pancreatic Microsomal Membranes, Promega; and Wheat Germ Extract, Promega. The kits and/or NPs provided herein can be provided with or used in conjunction with in vitro translation kits.

The nucleic acid to be translated (also referred to herein as target nucleic acid sequence) (typically mRNA) in the in vitro translation reaction can be selected by the user according to their needs and interest. The selected mRNA can be synthesized using routine techniques for producing mRNA. For example, mRNA of interest can be prepared by transcribing it from the DNA using in vitro transcription kits, such as PROTEINscript II T7 Kit (Ambion).

The NP-conjugates provided herein can be incubated with the mRNA of interest, for example, right before addition of the translation mix, or can be incubated with the translation mix prior to addition of the mRNA, or the NP-conjugates, mRNA, and translation mix can be mixed together.

In some embodiments of the methods provided herein, an NP conjugate is contacted with the target nucleic acid sequence and with a reagent for conducting in vitro translation (such as a commercially obtained in vitro translation kit). The mixture is incubated under conditions suitable to allow in vitro translation, and the protein or polypeptide product is detected.

The protein or polypeptide can be detected using any suitable means of detection. For example, where the protein or polypeptide is fluorescent, the protein or polypeptide is detected by exciting the sample with a suitable wavelength of light and the excitation is measured at a suitable emission wavelength. Methods of detecting proteins are well known in the art and include antibody based methods, such as enzyme linked immunosorbant assay using antibody that is capable of binding the protein or polypeptide, enzyme assays using a substrate that produced a detectable product, where the protein or polypeptide is expected to have enzymatic activity.

Exemplification

Methods

RNase Free treatment

RNase-free water was either purchased or prepared by incubating de-ionized water with 0.1% Diethyl pyrocarbonate (DEPC) and autoclaving. Only RNase-free water was used for all of the experiments.

Gold (Au) Nanoparticle (NP) Synthesis

Gold nanoparticles (NPs) were prepared as described herein. The particles ranged in size from 1-20 nm in diameter. Nanoparticles were soluble in water and buffer and stable due to surface coating ligands, such as (bis(p-sulfonatophenyl) phenylphosphine dihydrate, dipotassium salt (BPS).

Au NPs (~9.6 nm) were synthesized by reduction of $HAuCl_4$. For 100 ml synthesis, in mixture A, 79 ml of water and 1 ml of 1% $HAuCl_4.xH_2O$ were mixed and heated on a bench-top hot plate. In mixture B, 16.8 ml of water, 3 ml of 1% sodium citrate (reducing agent), 100 µl of 1% tannic acid (nucleating agent), and 100 µl of 0.265% sodium carbonate were mixed and heated. When the temperature of the mixtures reached 60° C., they were mixed together quickly and then stirred for 10 min at the same temperature. At the beginning the color of the solution was purple but changed to red as the reaction continued. After 10 min the solution was removed from the hot plate and cooled to room temperature. About two hours later a pinch amount of BPS (bis(p-sulfonatophenyl) phenylphosphine), negatively charged ligand, was added and gently stirred for several hours.

To separate the NPs from the solution, sodium chloride was added to the solution to raise the ionic strength of the solution, causing aggregation of the Au NPs due to charge screening. The solution was centrifuged the sediment of aggregated Au NPs at the bottom of spin tubes was collected. The supernatant was discarded and the sediment was re-dispersed in ~200 µl of pure water. For further purification, the particles were placed in a 1-1.5% agarose gel with 0.5×TBE and subject to 3-4 V/cm of electric field. Once the band of particles migrated a few centimeters, the band was cut out and placed into several milliliters of 0.5×TBE (45 mM tris, 45 mM boric acid, and 1 mM EDTA). After 1-2 days, most of the particles diffused from the gel piece into the TBE buffer. The solution was centrifuged to achieve a dark red Au NP layer at the bottom of the spin tubes. The layer was collected and filtered with 0.2 µm spin columns to get rid of impurities.

The average size of the particles was obtained by analysis of transition electron micrograph (TEM) images. Concentration of stock Au NP solution is calculated from the peak of absorption spectra, by using Beer-Lambert law. The size of the NP can be changed using methods known in the art, for example, by varying the amount of tannic acid. Smaller NPs are achieved when more of tannic acid is used.

Au NP—mPEG Functionalization

BPS coated Au NPs were incubated at room temperature in mPEG-SH (methoxypolyethylene glycol thiol, MW=356.5 g/mol) bath for ~24 hours with different ratios of Au NP:mPEG-SH (e.g. 1:200) at an Au NP concentration [Au NP] of $5 \times 10^{-7}$ M, allowing thiol linkages to form between the Au NP and the mPEG molecules. The solution was centrifuged with a bench-top micro-centrifuge at 10 k rpm for 30 min, and then the thick colored bottom layer was collected and resuspended in fresh 0.5×TBE. The centrifugation/resupension step was repeated at least 3 times to remove free mPEG molecules.

Au NP—DNA Conjugation

NPs were chemically linked to DNA having a sequence that is complementary to an mRNA of interest (such as mRNA encoding GFP or mRNA encoding mCherry). The DNA had a terminal thiol (on either the 5' or 3' end), which allowed the DNA to form a covalent bond with the gold NP upon simple incubation.[1-3] Au NPs were lyophilized with the thiol-functionalized DNA at a given Au NP:DNA ratio (for example ~1:100) and incubated in ~1×TBE for 2 days. DNA was incubated in 50 mM TCEP (tris(2-carboxyethyl)phosphine) for 1 hour before use. Free DNA strands were removed by centrifugation and resuspension as described above for mPEG functionalization.

NP:DNA ratios (also referred to herein as coverage, the average number of DNA strands per NP) were determined by chemical displacement of the DNA from the NP surface, separating the bare NPs from the DNA, and quantifying the amount of DNA by fluorescence spectroscopy.[4] The DNA strands were completely displaced from the Au NP by incubating the NP-DNA in concentrated MCH (6-Mercapto-1-hexanol) solution (~1-100 mM MCH) for extended time (~24 hours). Aggregated bare NPs were removed by centrifugation (~13 k rpm, 30 min), and the supernatant was mixed with a commercial dye (CYBR gold, Invitrogen) that allows the detection of nucleic acid strands in solution. Fluorescence emission intensity at 520 nm (excited at 490 nm) was measured. Concentration of DNA was determined by comparing fluorescence intensity of the DNA solutions with known concentrations of DNA.

The amount of DNA on the NP surface was varied by varying the incubation ratio of NP:DNA. The NP-DNA conjugates were purified from free DNA by spin centrifugation. In order to ensure that there were no free NPs, the reaction was performed with a large excess of DNA.

Transcription/Translation

The genes of interest (e.g. fluorescent gene such as eGFP and mCherry) were inserted into plasmid DNA. The standard T7 promoter was inserted during DNA replication using Taq DNA polymerase. Replicated DNA was amplified by polymerase chain reaction (PCR) and the products were purified with a commercial kit (QIAquick PCR Purification Kit, Qiagen). The concentration of DNA was determined by measuring optical absorbance at 260 nm. mRNA was transcribed from the plasmid DNA and purified using a commercial kit PROTEINscript II T7 Kit (Ambion). Template DNA remaining in the solution was removed by adding DNase (RNase-free DNase kit (Qiagen)). mRNA was purified from transcription kit components using RNEasy Mini Kit (Qiagen). Purified mRNA content was quantified by optical absorbance at 260 nm and stored at −80° C.

mRNA was used as template in the in vitro translation reaction with a commercial reticulocyte lysate kit (Retic Lysate IVT™ Kit (Ambion)), which was optimized for 0.1-1 µg of mRNA according to the manufacturers instructions. A fixed amount of mRNA (e.g. 0.25 µg per batch) was used for translation, with or without adding the NP or NP conjugates described herein Experiments were done under conditions to minimize the effects of RNase by keeping all the samples and tools clean. The ratio of NP or NP conjugated to mRNA ([Au NP]:[mRNA]) was varied from 0 to 1.

The NP-DNA conjugates were incubated with the mRNA and the translation mix was added. Following addition of the translation mix, protein expression and its quantification was performed using standard techniques, such as those described by the translation mix kits. For example, where the mRNA encodes GFP, expression was quantified by measuring the fluorescence of the sample at the peak GFP emission wavelength ($\lambda_{excitation}$=488 nm, $\lambda_{emission}$=510 nm. For mCherry, $\lambda_{excitation}$=587 nm and $\lambda_{emission}$=610 nm.

The resultant solution was subject to fluorescent measurement of the respective fluorescent gene product, which indicates the degree of gene expression. A background scan of the translation reaction in the absence of mRNA substrate was subtracted from the scans of translation reactions in the presence of mRNA substrate to determine net fluorescence contribution from synthesized protein.

Results

Enhancement of mRNA Expression in the Presence of NP-DNA Conjugates, and not the Presence of NP or DNA Alone.

Figure 4:
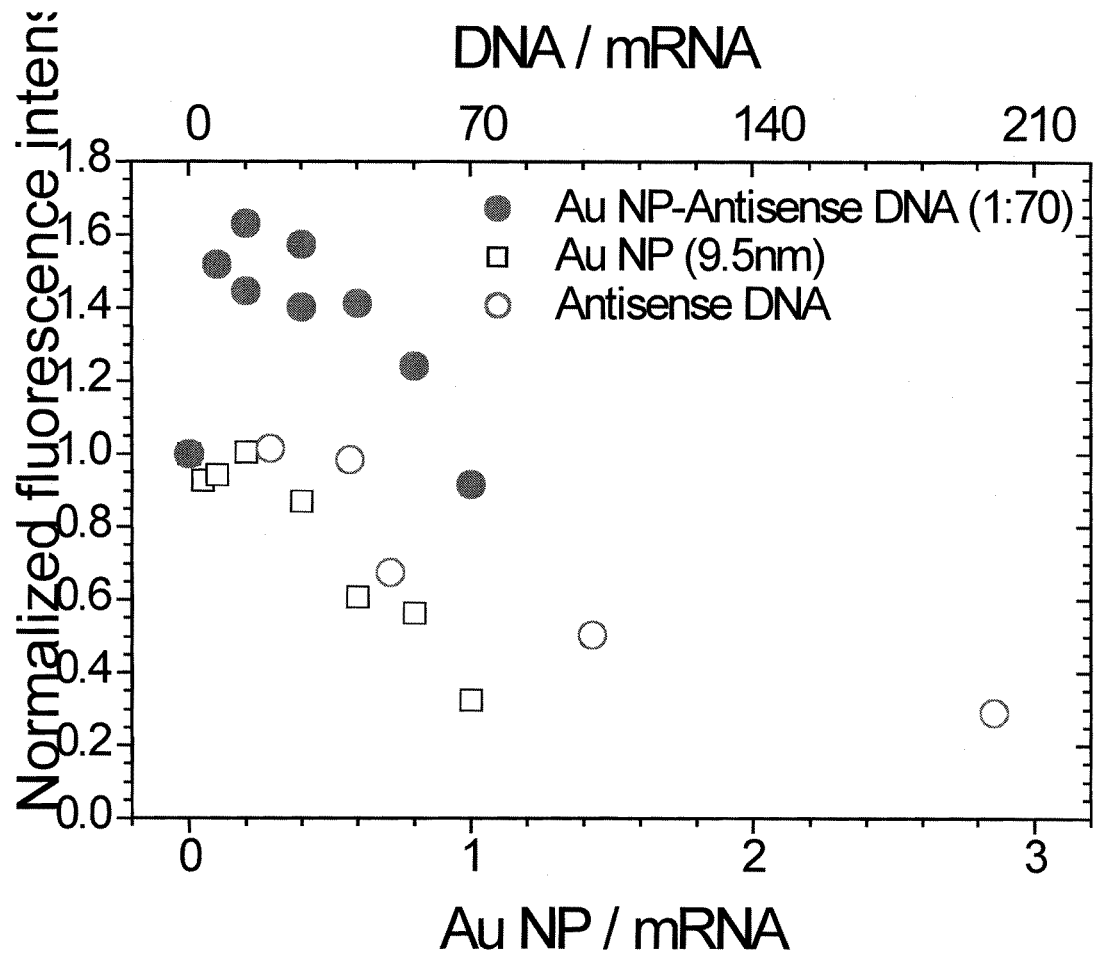
FIG. 4 is a graph showing expression of GFP as a function of DNA (open circles, x-axis is top line), NP (squares), and NP-DNA (filled circles) concentrations; expression was normalized to the amount where there was no DNA, NP, or NP-DNA (concentration=0 NP/mRNA or DNA/mRNA).

FIG. 4 shows the amount of Green Fluorescent Protein (GFP) expression when in vitro translation was carried out in the presence of an NP-conjugate. In this experiment, the conjugated compound was a DNA molecule having the sequence of SEQ ID NO. 3 (5'-HS-TTTTT TTTTT CTTGC TCACC ATGGT-3') that is capable of hybridizing to the GFP mRNA near the Kozak sequence. The NP had an average diameter of 9.5 nm and had and average of 70 strands of DNA conjugated thereto (filled circles). As shown in FIG. 4, the amount of GFP expression varied with increasing NP-conjugate concentration. Expression was higher than in the absence of NP-conjugates, about 1.6× the amount of expression in the absence of NP-conjugates. This enhancement of expression occurred for a NP-conjugate concentration range of <1 NP:mRNA. If the DNA alone was incubated with the mRNA, suppression of GFP expression was observed (open circles, x-axis is top axis, DNA/mRNA). Also, if unconjugated (bare) NPs of the same size were incubated with the mRNA, suppression of GFP expression was observed (squares).

Figure 5:
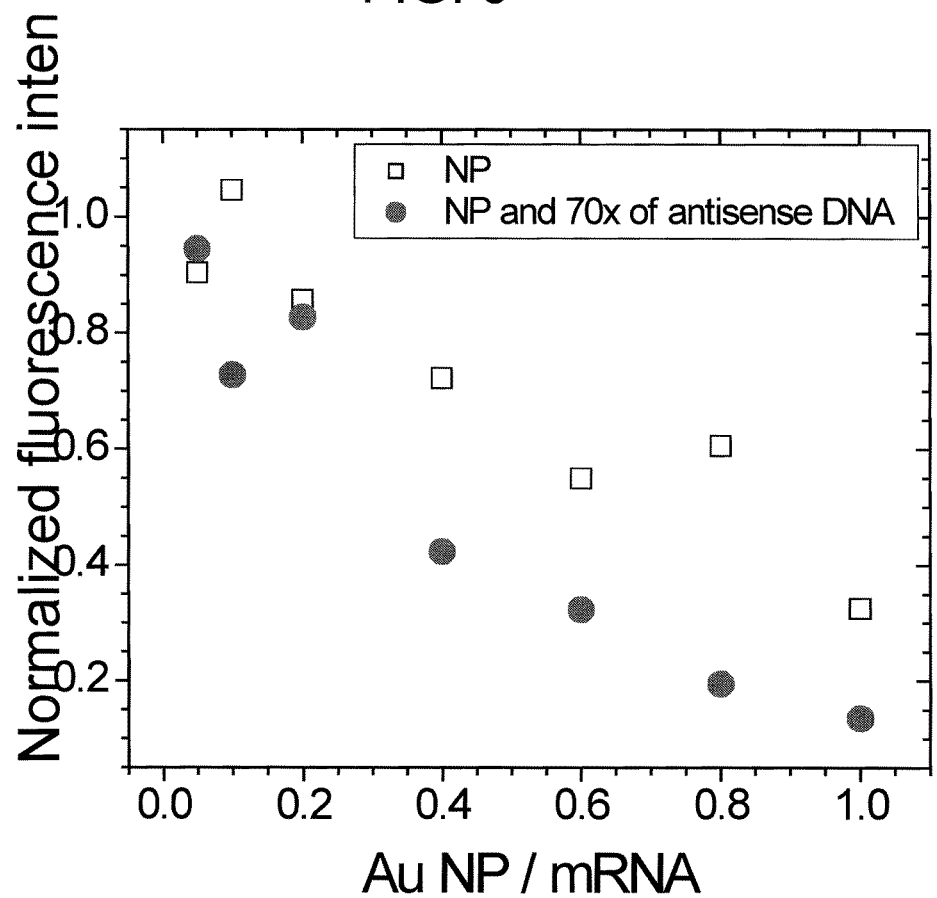
FIG. 5 is a graph showing expression of GFP in the presence of NPs that are not linked to the conjugate.

FIG. 5 shows expression of GFP in the presence of NPs that are not linked to the conjugate (in this case, DNA), (circles). As shown in FIG. 5, expression of GFP was suppressed in the presence of NP and DNA that were not conjugated, similar to NP in the absence of DNA (squares).

FIG. 6 shows the mRNA encoding mCherry and an example of sequences that would allow strong 42 or weak 40 binding to a homologous DNA sequence. For example a DNA molecule having the sequence of SEQ ID NO. 1 (5'-HS-TTTTT TTTTT CTCGT TGGGG TCTTT-3') is expected to show strong binding to the homologous mCherry mRNA sequence, having a ΔG of −18 kcal/mol. A DNA molecule having the sequence of SEQ ID NO. 2 (5'-HS-TTTTT TTTTT GATGT TGACG TTGTA-3') is expected to show weak binding to the homologous mCherry mRNA sequence, having a ΔG of −25.2 kcal/mol.

Figure 7:
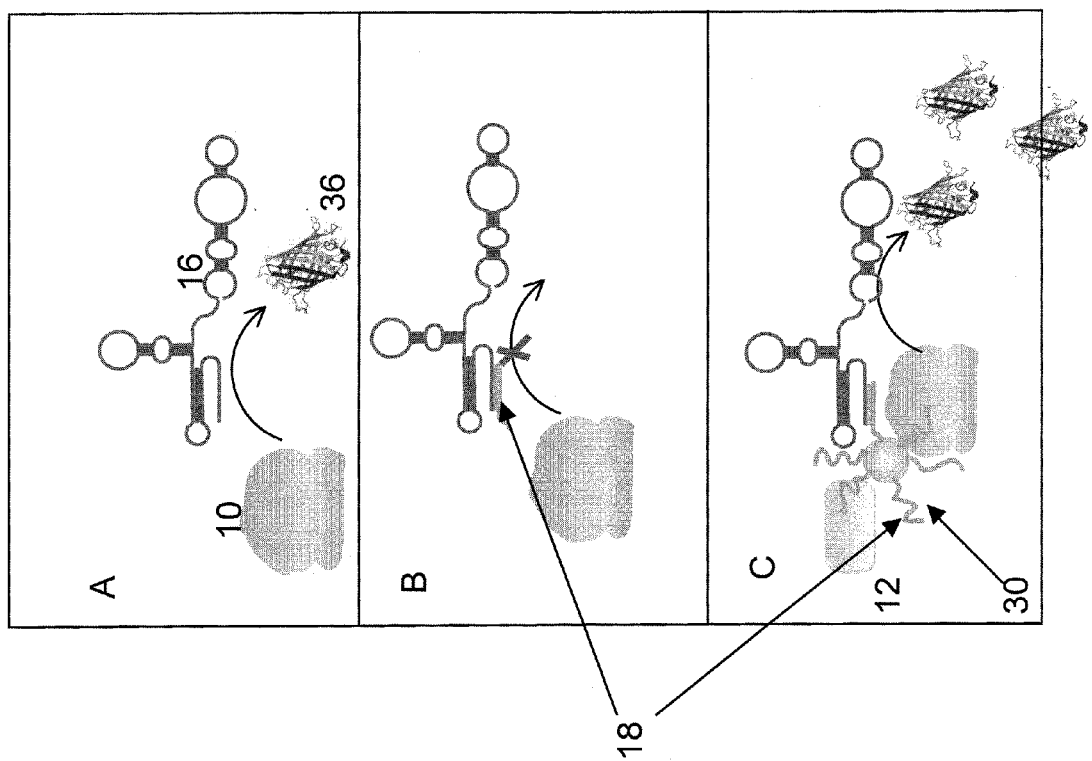
FIG. 7 is a schematic diagram showing the process of in vitro translation under control conditions (A), in the presence of unconjugated DNA (B), and in the presence of NP-DNA conjugates.

FIG. 7A-7C shows a schematic diagram of translation in various reaction mixtures. In FIG. 7A shows regular in vitro translation in the presence of ribosomes 10 and mRNA 16, producing protein product 36. FIG. 7B shows in vitro translation similar to FIG. 7A with the addition of DNA 18, which is capable of hybridizing to the mRNA. FIG. 7C shows in vitro translation similar to FIG. 7A, with the addition of NP-conjugates 30, where the conjugated compound is DNA 18 that is capable of hybridizing to the mRNA. As shown in FIG. 7A, the ribosome 10 translates the mRNA 16 to produce protein 36 that is encoded by the mRNA. When DNA 18 that is capable of hybridizing to the mRNA 16 is added (FIG. 7B) the DNA can hybridize to the mRNA and interfere with translation. When NP-conjugates 30 having DNA 18 that is capable of hybridizing to the mRNA 16 is added, additional components such eIFs 12 can be recruited, and the complex of transcription components 10, 12, and 16 is stabilized, resulting in more protein product 36.

Figure 8:
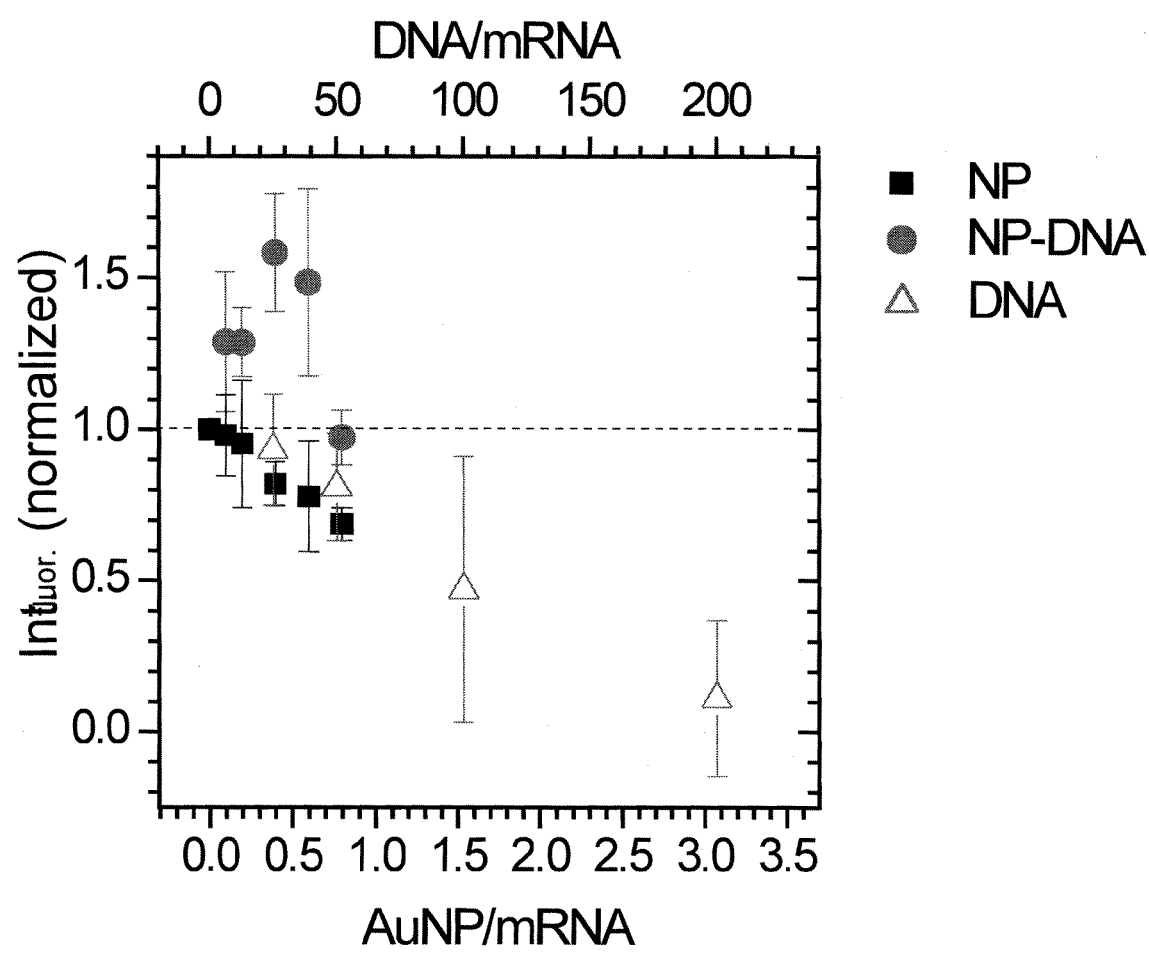
FIG. 8 is a graph showing expression of mCherry in the presence of unconjugated DNA (triangles), in the presence of NP (squares), and in the presence of NP-DNA conjugates (circles).

FIG. 8 shows that NP-DNA enhances translation 65% (circles) compared to translation in the absence of NP, DNA, or NP-DNA), and that NP (squares) or DNA alone (triangles) inhibited translation. Thus, attachment of the DNA to the NP changes the biophysical behavior of DNA in the in vitro translation reaction. In this experiment, the mRNA encoded mCherry, the DNA sequence was SEQ ID NO. 1, the NP had an average diameter of 9.5 nm, and the ratio of NP to DNA molecules was 1:65. NP-DNA conjugates were added at a concentration of <1 NP-DNA conjugate per mRNA molecule (bottom x-axis). The translation components were supplied in the form of rabbit reticulocyte lysate rabbit reticulocyte lysate kit (Retic Lysate IVT™ Kit (AM1200, Ambion))

Figure 9:
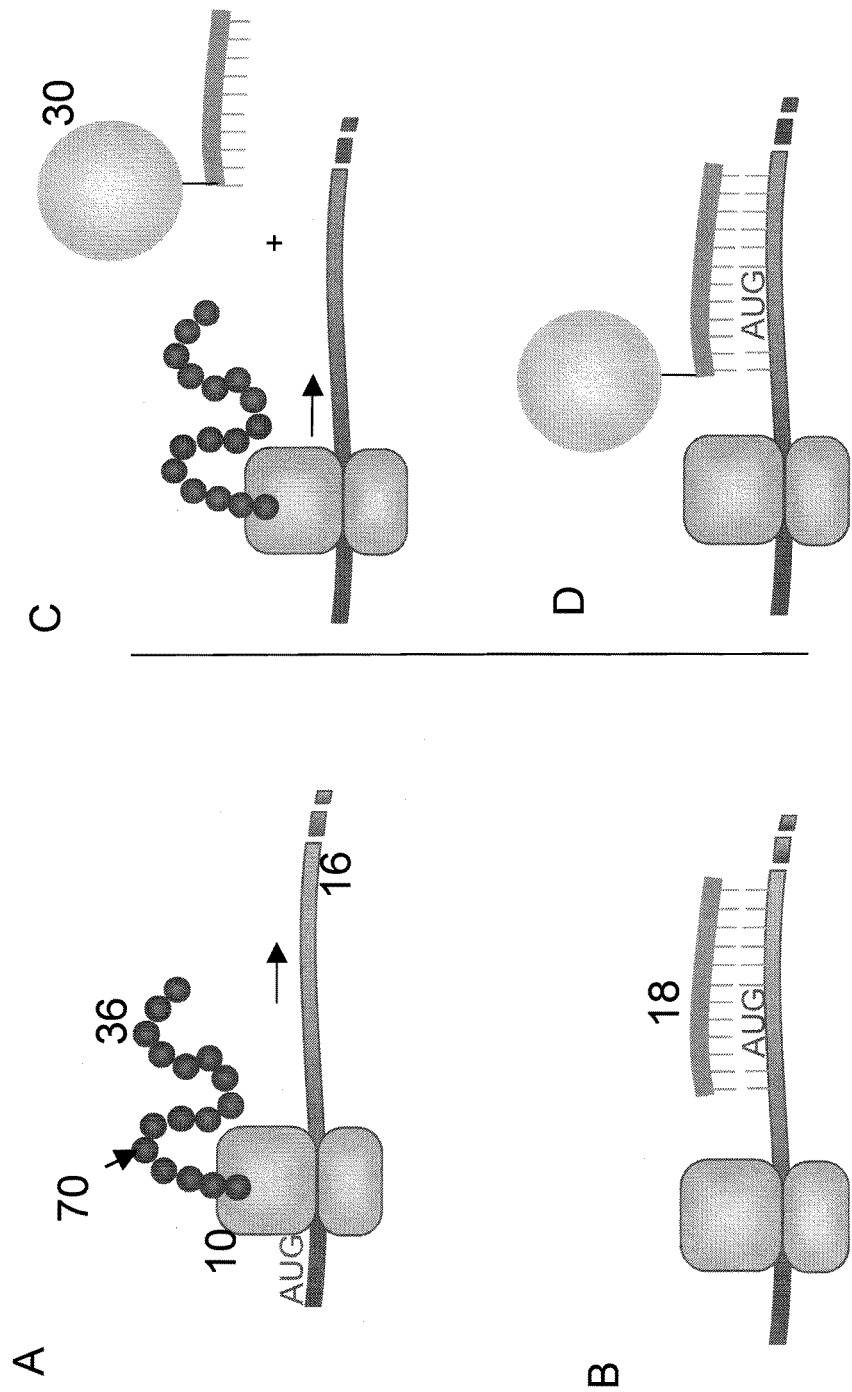
FIG. 9 is a schematic diagram showing a close up of the process of translation.
Figure 10:
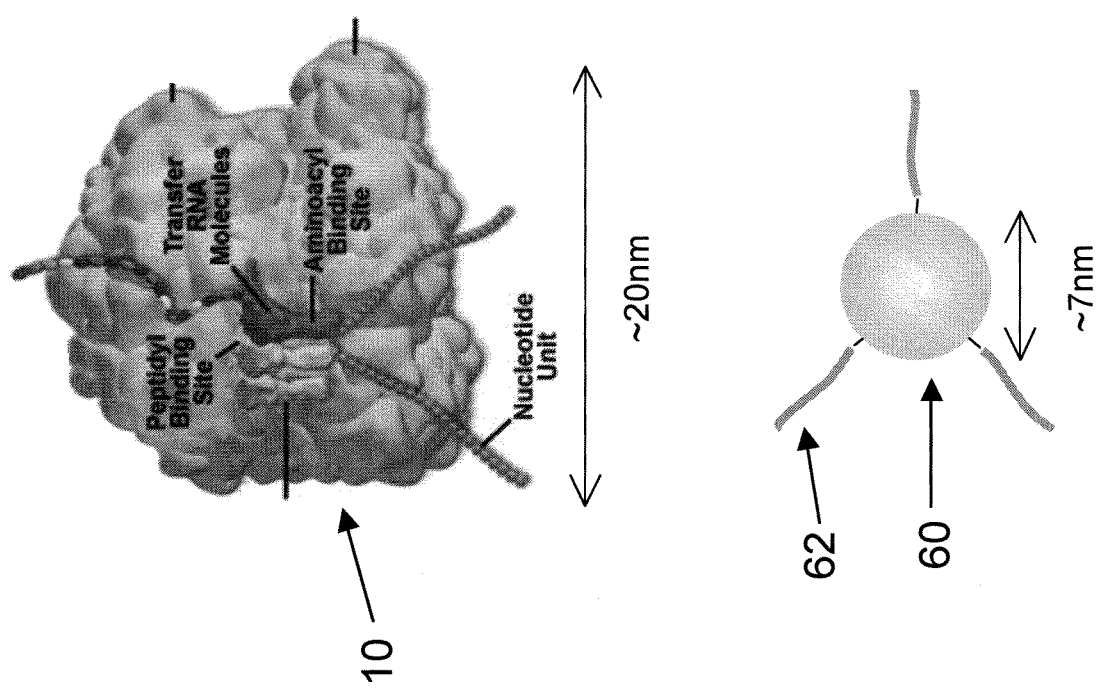
FIG. 10 is a schematic diagram showing a comparison of the size of a ribosome and the size of an NP-DNA conjugate.

The finding that NP-conjugates enhance in vitro translation was unexpected because it was thought that the NP-conjugates would sterically block the ribosome from traveling down the mRNA while translating, thereby inhibiting protein production. As shown in FIG. 10, the ribosome 10 is about 20 nm in diameter. An NP having a diameter of 7 nm 60 that is conjugated to DNA molecules of 10 bases in length 62 is has about the same diameter as a ribosome. As shown in FIG. 9A, during regular translation, the ribosome 10 binds to the mRNA 16 and translates the mRNA codons into amino acids 70, producing a protein 36, commencing at the AUG start codon of the mRNA. As shown in FIG. 9B, when a nucleic acid sequence 18 complementary to the mRNA is added, no protein is produced because the nucleic acid sequence 18 hybridizes to the mRNA and blocks the ribosome. FIG. 9 shows the position of the AUG start codon, however, the DNA does not need to hybridize to the AUG in order to interfere with protein production. As shown in FIG. 10, the NP-conjugates provided herein are of similar size as the ribosome. Therefore, as shown in FIGS. 9C and 9D, it was expected that like the nucleic acid sequence 18 of FIG. 9B, that the NP-DNA conjugate would block the ribosome 10 and that no or less protein would be produced.

As shown in FIG. 11, the suppression of protein production by free NP was not due to quenching of the fluorescent protein product 36. In this experiment, in vitro translation was carried out with mCherry mRNA. After in vitro translation was carried out, NP 24 at the indicated NP to mRNA ratios was added. As shown in FIG. 11, addition of NP after in vitro translation did not decrease the level of fluorescence, demonstrating that the NP does not cause quenching of the mCherry protein.

The NP-Nucleobase conjugate also binds with the translational machinery, most likely through electrostatic effects, as the DNA is negatively charged. While not wishing to be bound by theory, this interaction is thought to bring the mRNA, ribosome, and translational machinery in close proximity, enhancing translation. As shown in FIG. 12, NP and NP-DNA conjugates bind to proteins in the translation mix. In this experiment, NP or NP conjugates were incubated with the reticulocyte lysate mix. All of the samples were incubated at 30° C. for 1 hr before loading onto a 1.5% agarose gel, and subjected to 72V/18.5 cm for 90 min. The NP had an average diameter of 9.5 nm. NP-DNA conjugates were prepared as described herein with a Low Coverage of DNA molecules per particle (27 DNA molecules per NP) and High Coverage of DNA molecules per particle (65 DNA molecules per NP). The lanes of the gels of FIG. 12 are as follows: 1. reticulocyte lysate mix; 2. NP; 3. NP-mPEG; 4. NP-DNA Low Coverage; 5. NP-DNA High Coverage; 6, 7, 8 and 9: mix of 1&2, 1&3, 1&4 and 1&5, respectively.

Tunable Enhancement

Figure 13:
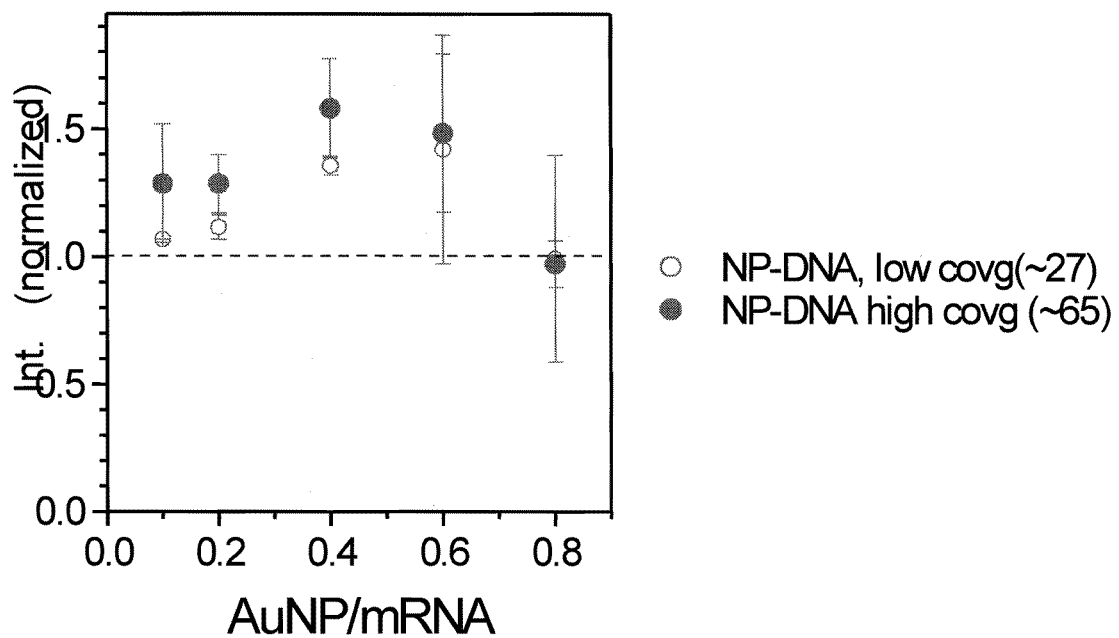
FIG. 13 is a graph of the results of in vitro translation conducted with NP-DNA having high coverage (filled circles) and low coverage (open circles) of DNA molecules.

As shown in FIG. 13, the amount of translation enhancement varies with coverage, which is ratio of conjugated compound molecules per NP and also varies with the ratio of NP conjugate to mRNA. NP-DNA High Coverage (filled circles) and Low Coverage (open circles) were prepared as described for FIG. 12. The indicated amount of NP-DNA per mRNA was incubated with mRNA and translation mix as described herein.

Figure 14:
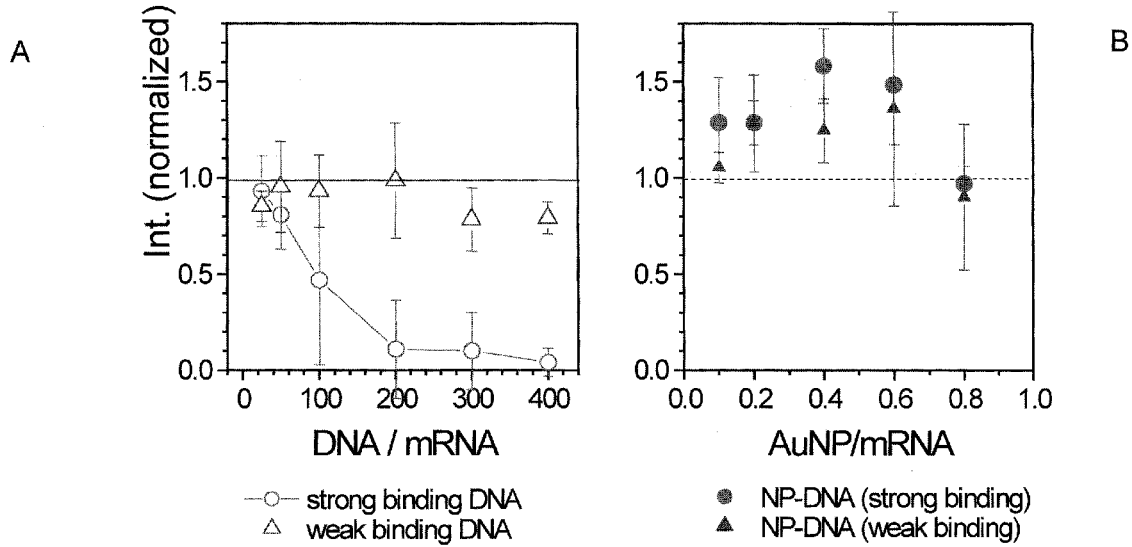
FIG. 14 shows two graphs of results of in vitro translation conducted with DNA having strong binding (circles) and weak binding (triangles) to the mRNA when added to the reaction as free DNA (A) and as NP-DNA conjugates (B).

As shown in FIG. 14, NP-conjugates having DNA sequences that bind more strongly to the mRNA exhibit increased translation enhancement compared to NP-conjugates having DNA sequences that bind more weakly to the mRNA; however, even the NP-conjugates having weak binding DNA enhances transcription of the mRNA.

SEQ ID NO. 1 and SEQ ID NO. 2 were conjugated to NP as described herein at a reaction ratio of NP:DNA=1:160. The NP had an average diameter of 9.5 nm. FIG. 14A shows the results of control reactions run in the presence of unconjugated DNA having SEQ ID NO. 1 (strong binding, circles) or unconjugated DNA having SEQ ID NO. 2 (weak binding, triangles). FIG. 14B shows the results of reactions run using NP-DNA having SEQ ID NO. 1 (circles) and NP-DNA having SEQ ID NO. 2 (triangles) at the indicated ratio of NP-DNA conjugate to mRNA.

Translation of Specific Genes from a Pool can be Enhanced.

Figure 15:
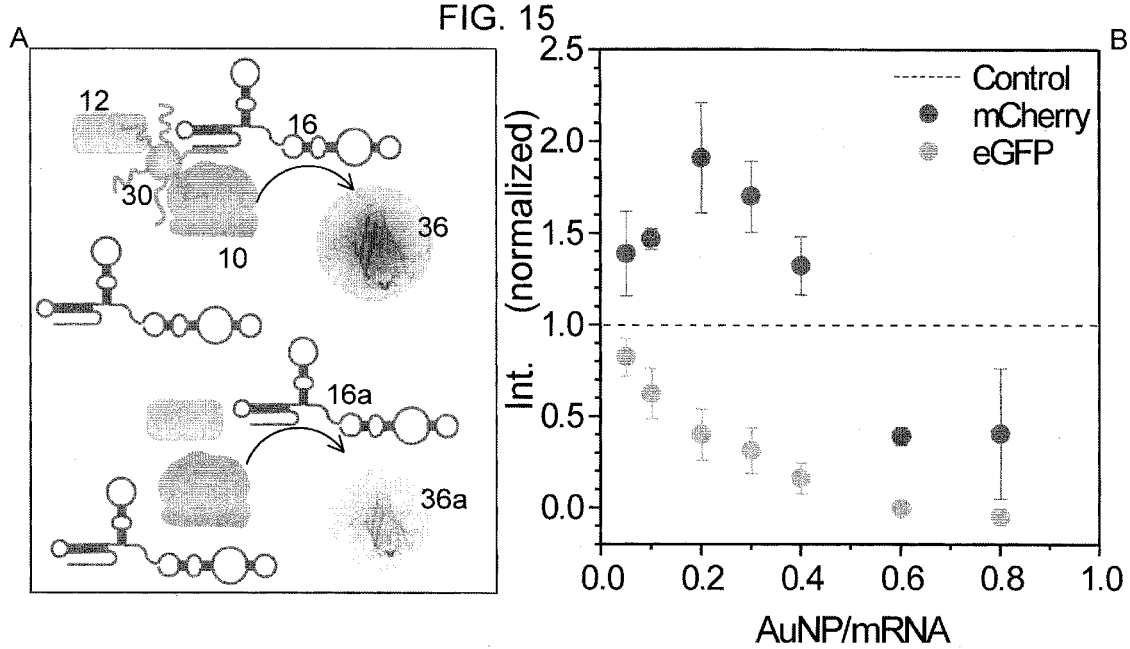
FIG. 15 is a schematic (A) and a graph of the results (B) of an in vitro translation reaction conducted in the presence of a mixture of two different species of mRNA and NP-DNA having a DNA that is capable of binding one of the species of mRNA.

SEQ ID NO. 1 was conjugated to NP as described herein at a reaction ratio of NP:DNA=1:160. The NP-DNA conjugates were introduced to a mixture of mRNA molecules (encoding mCherry and GFP at the same concentrations) at the indicated ratios of NP-DNA complexes to mRNA. Protein production was measured by detecting fluorescence of the mCherry protein and GFP, respectively, which are distinguishable by color. A schematic diagram of the reaction mixture is shown in FIG. 15A. For translation of mCherry mRNA 16, the NP-DNA interacts with ribosomes 10, eIFs 12, and the mRNA 16, to produce mCherry protein. For translation of GFP mRNA 16a, the ribosome 10 and eIFs 12 interact with the mRNA 16a to produce GFP 36a. As shown in FIG. 15B, mCherry protein was specifically enhanced over GFP, and the expression of GFP was suppressed demonstrating that the NP-DNA conjugates and methods provided herein can be used to enhance translation of specific genes from a mixture of mRNA species.

Translation Enhancement with Other Conjugates

As shown in FIG. 16, other conjugates such as thiolated PEG can also enhance transcription. NPs were conjugated to mPEG as described herein. The reaction mixtures contained ratios of mPEG to NP of 200, 1000, and 2000. As shown in FIG. 16, use of NP-mPEG conjugates 80 in the in vitro translation reaction results in a ~25% enhancement in protein production compared to a control reaction which was conducted in the absence of NP-mPEG. The enhancement is shown for two different mRNAs, mCherry, FIG. 16A and GFP, FIG. 6B.

REFERENCES

1. S. Park, K. A. Brown, and K. Hamad-Schifferli, Changes in oligonucleotide conformation on nanoparticle surfaces by modification with mercaptohexanol, *Nano Letters* 4, 1925-1929 (2004).
2. D. Zanchet et al., Electrophoretic isolation of discrete Au nanocrystal/DNA conjugates, *Nano Letters* 1, 32-35 (2001).
3. D. Zanchet et al., Electrophoretic and Structural Studies of DNA-Directed Au Nanoparticle Groupings, *Journal of Physical Chemistry B* 106, 11758-11763 (2002).
4. L. M. Demers et al., A Fluorescence-Based Method for Determining the Surface Coverage and Hybridization Efficiency of Thiol-Capped Oligonucleotides Bound to Gold Thin Films and Nanoparticles, *Analytical Chemistry* 72, 5535-5541 (2000).
5. Fraser, C. S. and J. A. Doudna, Structural and Mechanistic Insights into Hepatitis C Viral Translation Initiation. Nature Reviews Microbiology 5: 29-38 (2007).

While the technology has been particularly shown and described with reference to specific embodiments, it should be understood by those skilled in the art that various changes in form and detail may be made therein without departing from the spirit and scope of the technology as defined by the appended claims.

---

What is claimed is:

1. A method for in vitro translation of an mRNA sequence of interest comprising contacting nanoparticles with an mRNA sequence of interest to be translated, and with reagents to cause in vitro translation, wherein the nanoparticles are conjugated to a nucleobase sequence selected from the group consisting of an RNA sequence, a DNA sequence and a PNA sequence, wherein the nucleobase sequence is complementary to at least a portion of the mRNA sequence, thereby resulting in translation of the mRNA of interest.

2. The method of claim 1, wherein the nanoparticles are first contacted with the reagents and incubated prior to addition of the mRNA sequence of interest.

3. The method of claim 1, wherein the nanoparticles are first contacted with the mRNA sequence of interest and incubated prior to addition of the reagents.

4. The method of claim 1, wherein the nanoparticles are contacted with the mRNA sequence of interest at a ratio of less than one nanoparticle per mRNA sequence.

5. A method for in vitro translation of an mRNA sequence of interest comprising contacting nanoparticles with the mRNA sequence of interest to be translated, and with reagents to cause in vitro translation, wherein the nanoparticles are coated with PEG chains, thereby resulting in translation of the mRNA of interest.

6. The method of claim 5, wherein each nanoparticle is coated with about 10 to 200 PEG chains.

7. The method of claim 5, wherein the nanoparticles are further conjugated to a nucleobase sequence selected from the group consisting of an RNA sequence, a DNA sequence, and a PNA sequence, wherein the nucleobase sequence is complementary to at least a portion of the mRNA sequence.

8. The method of claim 1 or 5, wherein the nanoparticles comprise gold.

9. The method of claim 1 or 5, wherein the nanoparticles have a mean diameter of 5-25 nm.

10. The method of claim 1 or 5, wherein the nanoparticles have a mean diameter of 10 nm.

11. The method of claim 1 or 7, wherein the nucleobase sequence comprises a DNA sequence.

12. The method of claim 1 or 7, wherein the nucleobase sequence comprises an RNA sequence.

13. The method of claim 1 or 7, wherein the nucleobase sequence comprises a PNA sequence.

14. The method of claim 1 or 7, wherein the nucleobase sequence is complementary to a non-translated portion of the mRNA sequence.

15. The method of claim 1 or 7, wherein the nucleobase sequence is complementary to the Kozak Sequence.

16. The method of claim 1 or 7, wherein the nucleobase sequence comprises a poly T sequence.

17. The method of claim 1 or 7, wherein the nucleobase sequence is 10 to 50 bases in length.

18. The method of claim 1 or 7, wherein each nanoparticle is conjugated to 10 to 100 nucleobase sequence strands.

19. The method of claim 1 or 7, wherein each nanoparticle is conjugated to 20 to 70 nucleobase sequence strands.

* * * * *

SEQUENCE LISTING

```
<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: strong binding to the homologous mCherry mRNA
      sequence

<400> SEQUENCE: 1
tttttttttt ctcgttgggg tcttt                                          25

<210> SEQ ID NO 2
<211> LENGTH: 25
<212> TYPE: DNA
<213> ORGANISM: Artificial Sequence
<220> FEATURE:
```

```
<223> OTHER INFORMATION: weak binding to the homologous mCherry mRNA
      sequence

<400> SEQUENCE: 2 ttttttttttt gatgttgacg ttgta                                          25

<210> SEQ ID NO 3
<211> LENGTH: 25
<212> TYPE: DNA
<213> ORGANISM: Artificial Sequence
<220> FEATURE:
<223> OTHER INFORMATION: GFP mRNA hybridizing sequence

<400> SEQUENCE: 3 ttttttttttt cttgctcacc atggt                                          25

<210> SEQ ID NO 4
<211> LENGTH: 731
<212> TYPE: RNA
<213> ORGANISM: Artificial Sequence
<220> FEATURE:
<223> OTHER INFORMATION: mCherry

<400> SEQUENCE: 4
gcuagcgcua ccggucgcca ccauggugag caagggcgag gaggauaaca uggccaucau      60
caaggaguuc augcgcuuca aggugcacau ggagggcucc gugaacgcc acgaguucga      120 gaucgagggc gagggcgagg gccgccccua cgagggcacc cagaccgcca agcugaaggu     180
gaccaagggu ggccccccugc ccuucgccug ggacauccug uccccucagu ucauguacgg    240
cuccaaggcc uacgugaagc accccgccga caucccccgac uacuugaagc uguccuuccc   300
cgagggcuuc aagugggagc gcgugaugaa cuucgaggac ggcggcgugg ugaccgugac    360
ccaggacucc ucccugcagg acggcgaguu caucuacaag gugaagcugc gcggcaccaa    420 cuucccccucc gacggccccg uaaugcagaa gaagaccaug ggcugggagg ccuccuccga    480
gcggauguac cccgaggacg gcgcccugaa gggcgagauc aagcagaggc ugaagcugaa    540
ggacggcggc cacuacgacg cugaggucaa gaccaccuac aaggccaaga agcccgugca    600
gcugcccggc gccuacaacg ucaacaucaa guuggacauc accucccaca acgaggacua    660
caccaucgug aacaguacg aacgcgccga gggccgccac uccaccggcg caluggacga    720 gcuguacaag u                                                         731

<210> SEQ ID NO 5
<211> LENGTH: 27
<212> TYPE: RNA
<213> ORGANISM: Artificial Sequence
<220> FEATURE:
<223> OTHER INFORMATION: mCherry sequence bound to SEQ ID NO: 1

<400> SEQUENCE: 5
gacggccccg uaaugcagaa gaagacc                                         27

<210> SEQ ID NO 6
<211> LENGTH: 29
<212> TYPE: RNA
<213> ORGANISM: Artificial Sequence
<220> FEATURE:
<223> OTHER INFORMATION: mCherry sequence bound to SEQ ID NO: 2

<400> SEQUENCE: 6
gccuacaacg ucaacaucaa guuggacau                                       29
```